(12) United States Patent
Marzabadi et al.

(10) Patent No.: US 7,446,204 B2
(45) Date of Patent: Nov. 4, 2008

(54) AMINO SUBSTITUTED ARYLOXYBENZYLPIPERIDINE DERIVATIVES

(75) Inventors: Mohammad R. Marzabadi, Ridgewood, NJ (US); Chien-An Chen, Flushing, NY (US); Yu Jiang, Jersey City, NJ (US); Kai Lu, Lake Hiawatha, NJ (US); Kim Andersen, Ridgewood, NJ (US)

(73) Assignee: H. Lundbeck A/S, Valby - Copenhagen (DK)

( * ) Notice: Subject to any disclaimer, the term of this patent is extended or adjusted under 35 U.S.C. 154(b) by 84 days.

(21) Appl. No.: 11/230,849

(22) Filed: Sep. 20, 2005

(65) Prior Publication Data

US 2006/0079524 A1    Apr. 13, 2006

Related U.S. Application Data

(60) Provisional application No. 60/616,965, filed on Oct. 8, 2004.

(51) Int. Cl.
*C07D 211/14* (2006.01)
*A61K 31/451* (2006.01)

(52) U.S. Cl. .................... 546/247; 514/315
(58) Field of Classification Search ............. 514/315; 546/247

See application file for complete search history.

(56) References Cited

U.S. PATENT DOCUMENTS

| | | | |
|---|---|---|---|
| 6,503,928 B2 | 1/2003 | Kelly et al. | |
| 6,727,264 B1 * | 4/2004 | Marzabadi et al. | 514/323 |
| 7,067,534 B1 | 6/2006 | Marzabadi et al. | |
| 2006/0079522 A1 * | 4/2006 | Marzabadi et al. | 514/235.2 |

FOREIGN PATENT DOCUMENTS

| | | |
|---|---|---|
| EP | 1 020 434 | 7/2000 |
| WO | WO 02/094799 | 11/2002 |
| WO | WO 2004/005257 | 1/2004 |
| WO | WO 2004/052848 | 6/2004 |

OTHER PUBLICATIONS

Browning, "Recent developments in the discovery of melanin-concentrating hormone antagonists:novel antiobesity agents", Expert Opinion in Therapeutic Patents, Mar. 2004, 14(3):313-325.
Carpenter & Hertzog, "Melanin-concentrating hormone receptor antagonists as potential antiobesity agents", Expert Opinion in Therapeutic Patents, Nov. 2002, 12(11):1639-1646.
Collins & Kym, "Prospects for obesity treatment: MCH receptor antagonists", Current Opinion in Investigational Drugs, Apr. 2003, 4(4):386-394.
Kowalski & McBriar, "Therapeutic potential of melanin-concentrating hormone-1 receptor antagonists for the treatment of obesity", Expert Opinion in Investigational Drugs, Sep. 2004, 13(9):1113-1122.
Takekawa, et al., "T-226296: a novel, orally active and selective melanin-concentrating hormone receptor antagonist", European Journal of Pharm., Mar. 2002, 438(3):129-135.

* cited by examiner

*Primary Examiner*—Kamal Saeed
*Assistant Examiner*—Shawquia Young
(74) *Attorney, Agent, or Firm*—Kitae Lim

(57) ABSTRACT

This invention is directed to Amino substituted Aryloxybenzylpiperidine derivatives which are ligands at the MCH1 receptor. The invention provides a pharmaceutical composition comprising a therapeutically effective amount of a compound of the invention and a pharmaceutically acceptable carrier. This invention also provides a pharmaceutical composition made by admixing a therapeutically effective amount of a compound of the invention and a pharmaceutically acceptable carrier. This invention further provides a process for making a pharmaceutical composition comprising combining a therapeutically effective amount of a compound of the invention and a pharmaceutically acceptable carrier. This invention also provides a method of treating a subject suffering from depression and/or anxiety which comprises administering to the subject a therapeutically effective amount of a compound of the subject invention. This invention also provides a method of treating a subject suffering from obesity which comprises administering to the subject a therapeutically effective amount of a compound of the subject invention.

7 Claims, No Drawings

AMINO SUBSTITUTED ARYLOXYBENZYLPIPERIDINE DERIVATIVES

This application claims the benefit of U.S. Provisional Application No. 60/616,965 filed Oct. 8, 2004, the contents of which are hereby incorporated by reference.

FIELD OF THE INVENTION

The present invention relates to compounds that are ligands at the MCH1 receptor, and as such are useful to treat depression, anxiety or obesity.

BACKGROUND OF THE INVENTION

Throughout this application, various publications are referenced to in full citations. The disclosures of these publications are hereby incorporated by reference into this application to describe more fully the state of the art to which this invention pertains.

Melanin-concentrating hormone (MCH) is a cyclic 19-amino acid peptide produced by neurons in the lateral hypothalamus and zona incerta of the brain. Mammalian MCH is conserved between rat, mouse, and human, exhibiting 100% amino acid homology, and the effects of MCH are mediated through receptors that belong in the rhodopsin superfamily of G protein-coupled receptors. Presently, two receptor subtypes for MCH have been identified in humans, MCH1 and MCH2.

The link between MCH1 and the effects of MCH on feeding was suggested by reports on the phenotype of the MCH1 knockout mice. Independent groups generated knock-out mice with the targeted deletion of the MCH1 receptor. The phenotype of these mice was lean, hyperphagic and hypermetabolic, with increased resistance to diet-induced obesity (D. J. Marsh, et al., *Proc. Natl. Acad. Sci.* 2002, 99, 3240-3245). These observations evidence that MCH1 antagonists are useful to treat obesity.

To further assess the physiological role of the MCH1 receptor, SNAP-7941, a selective MCH1 small molecule antagonist, was evaluated in several animal models (B. Borowsky, et al., *Nature Medicine,* 2002, 8, 825-830). Pharmacological blockade of the MCH1 receptor with SNAP-7941 produced a profile similar to clinically used anti-depressants and anxiolytics in behavioral models of depression and/or anxiety: the rat forced-swim, rat social interaction and guinea pig maternal-separation vocalization tests.

These observations evidence that MCH1 antagonists are useful to treat depression and anxiety.

Current treatments for depression, anxiety and obesity are on the market. However, numerous patients do not respond to current treatments. Hence, there remains the need for alternative methods of treatment.

SUMMARY OF THE INVENTION

The objective of the present invention is to provide compounds that are ligands at the MCH1 receptor. The present invention relates to compounds of Formula I.

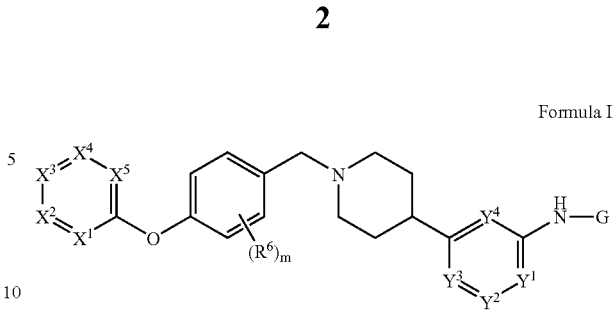

Formula I wherein each $X^1$, $X^2$, $X^3$, $X^4$ and $X^5$ is independently $CR^1$ or N, provided that if one X is N then the remaining X are each $CR^1$;

wherein each $Y^1$, $Y^2$, $Y^3$ and $Y^4$ is independently $CR^7$ or N, provided that if one Y is N then the remaining Y are each $CR^7$;

wherein G is hydrogen or —C(O)D;

wherein D is composed of one of the following moieties:

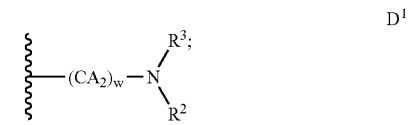

$D^1$

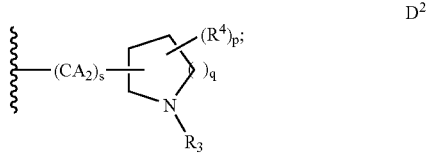

$D^2$

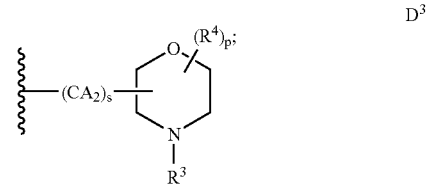

$D^3$

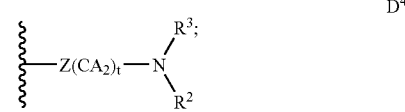

$D^4$

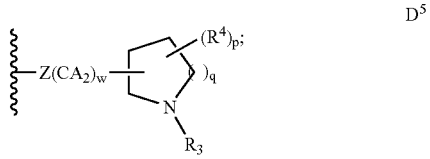

$D^5$

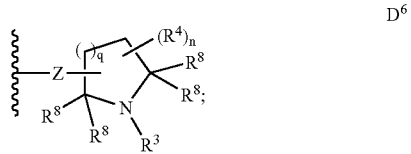

$D^6$

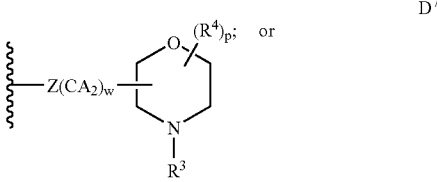

$D^7$

-continued

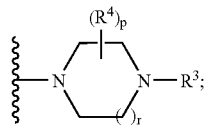

wherein Z is —N(R$^5$)— or —O—;
wherein each A is independently H or straight chained or branched C$_1$-C$_4$ alkyl;
wherein each R$^1$ is independently H, straight chained or branched C$_1$-C$_7$ alkyl, straight chained or branched C$_1$-C$_7$ fluoroalkyl, straight chained or branched C$_1$-C$_7$ alkoxy, F, Cl, Br or I;
wherein R$^2$ is H or straight chained or branched C$_1$-C$_4$ alkyl;
wherein R$^3$ is H or straight chained or branched C$_1$-C$_4$ alkyl;
or wherein the R$^2$ moiety, the nitrogen atom adjacent to the R$^2$ moiety, the R$^3$ moiety, and a bond formed between the R$^2$ moiety and the R$^3$ moiety form:

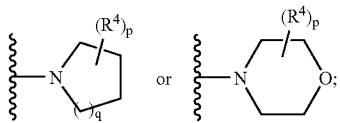

wherein R$^4$ is straight chained or branched C$_1$-C$_4$ alkyl, straight chained or branched C$_1$-C$_4$ fluoroalkyl or F;
wherein R$^5$ is H or straight chained or branched C$_1$-C$_4$ alkyl;
wherein each R$^6$ is independently straight chained or branched C$_1$-C$_7$ alkyl, straight chained or branched C$_1$-C$_7$ fluoroalkyl, straight chained or branched C$_1$-C$_7$ alkoxy, F, Cl, Br or I;
wherein each R$^7$ is independently H, straight chained or branched C$_1$-C$_7$ alkyl, straight chained or branched C$_1$-C$_7$ fluoroalkyl, straight chained or branched C$_1$-C$_7$ alkoxy, F, Cl, Br or I;
wherein R$^8$ is H, straight chained or branched C$_1$-C$_4$ alkyl, straight chained or branched C$_1$-C$_4$ fluoroalkyl or F;
wherein m is an integer from 0 to 4 inclusive;
wherein n is an integer from 0 to 2 inclusive;
wherein p is an integer from 0 to 4 inclusive;
wherein q is an integer from 0 to 3 inclusive;
wherein r is 1 or 2;
wherein s is an integer from 0 to 4 inclusive;
wherein t is an integer from 2 to 4 inclusive; and
wherein w is an integer from 1 to 5 inclusive;
or a pharmaceutically acceptable salt thereof.

In separate embodiments of the invention, the compound is selected from one of the specific compounds disclosed in the Experimental Section.

Furthermore, the present invention provides a pharmaceutical composition comprising a therapeutically effective amount of a compound of Formula I and a pharmaceutically acceptable carrier. The present invention also provides a process for making a pharmaceutical composition comprising admixing a therapeutically effective amount of a compound of Formula I and a pharmaceutically acceptable carrier.

Moreover, the present invention provides a method of treating a subject suffering from depression comprising administering to the subject a therapeutically effective amount of a compound of Formula I. The present invention further provides a method of treating a subject suffering from anxiety comprising administering to the subject a therapeutically effective amount of a compound of Formula I.

DETAILED DESCRIPTION OF THE INVENTION

Definitions

In the present invention, the term "straight chained or branched C$_1$-C$_7$ alkyl" refers to a saturated hydrocarbon having from one to seven carbon atoms inclusive. Examples of such substituents include, but are not limited to, methyl, ethyl, 1-propyl, 2-propyl, 1-butyl, 2-butyl, 2-methyl-2-propyl, 2-methyl-1-propyl and n-heptyl. Similarly, the term "straight chained or branched C$_1$-C$_4$ alkyl" refers to a saturated hydrocarbon having from one to four carbon atoms inclusive.

The term "straight chained or branched C$_1$-C$_7$ fluoroalkyl" refers to a saturated hydrocarbon having from one to seven carbon atoms inclusive substituted with one or more fluorine atoms. Examples of such substituents include, but are not limited to, trifluoromethyl, pentafluoroethyl, 1-fluoroethyl, 1,2-difluoroethyl and 3,4 difluoroheptyl. Similarly, the term "straight chained or branched C$_1$-C$_4$ fluoroalkyl" refers to a saturated hydrocarbon having from one to four carbon atoms inclusive substituted with one or more fluorine atoms per carbon atom.

The term "straight chained or branched C$_1$-C$_7$ alkoxy" refers to a saturated alkoxy group having from one to seven carbon atoms inclusive with the open valency on the oxygen. Examples of such substituents include, but are not limited to, methoxy, ethoxy, n-butoxy, t-butoxy and n-heptyloxy.

The specific compounds disclosed in the present invention are identified by their IUPAC names. The names of the compounds were generated using the program Chemistry 4-D Draw Nomenclator™ Database (Version 7.01c, ChemInnovation Software, Inc.). According to ChemInnovation Software Inc., Nomenclator™ automatically assigns systematic names to organic structures according to IUPAC nomenclature rules. Accordingly, this application discloses the Amino substituted Aryloxybenzylpiperidine derivatives encompassed by Formula I in accordance with IUPAC nomenclature rules.

For illustrative purposes, and without limiting the invention, the compound of example 1 k has the following structure:

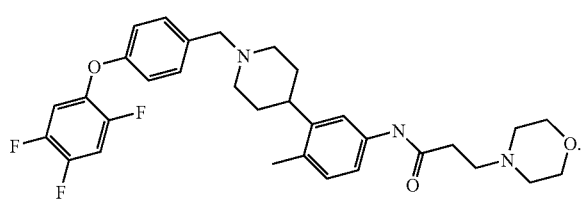

This compound is constructed from Formula I wherein each $X^1$, $X^2$, $X^3$, $X^4$ and $X^5$ is $CR^1$; wherein each $R^1$ is independently H or F; wherein m is 0; wherein each $Y^1$, $Y^2$, $Y^3$ and $Y^4$ is $CR^7$; wherein each $R^7$ is independently H or methyl; wherein G is —C(O)D; wherein D is $D^1$; wherein w is 2, wherein each A is H; and wherein the $R^2$ moiety, the nitrogen atom adjacent to the $R^2$ moiety, the $R^3$ moiety and a bond formed between the $R^2$ moiety and the $R^3$ moiety join together to form:

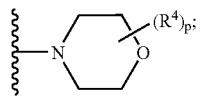

and wherein p is 0.

Additionally, the invention further provides certain embodiments of the present invention that are described below.

In one embodiment of the invention of Formula I, the compound has the structure:

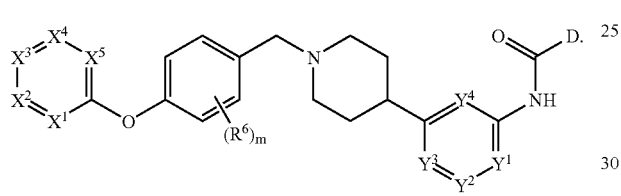

In another embodiment, D is

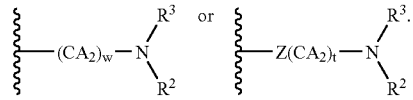

In another embodiment, D is

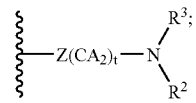

and Z is —N(R$^5$)—.

In another embodiment, t is 2 or 3 and $R^2$ is H, methyl or ethyl.

In another embodiment, D is

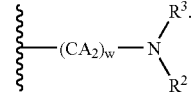

In another embodiment, w is 1 or 2, and $R^3$ is H, methyl or ethyl.

In another embodiment, $R^2$ is H, methyl or ethyl.

In another embodiment, the $R^2$ moiety, the nitrogen atom adjacent to the $R^2$ moiety, the $R^3$ moiety, and a bond formed between the $R^2$ moiety and the $R^3$ moiety form:

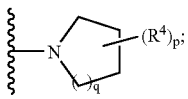

and p is 0.

In another embodiment, the $R^2$ moiety, the nitrogen atom adjacent to the $R^2$ moiety, the $R^3$ moiety, and a bond formed between the $R^2$ moiety and the $R^3$ moiety form:

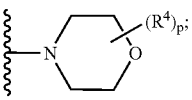

and p is 0.

In another embodiment, D is

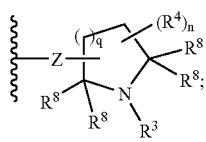

n is 0 and $R^3$ is H or methyl.

In another embodiment, D is

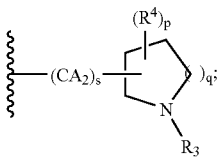

p is 0 and $R^3$ is H or methyl.

In another embodiment, s is 0 or 1.

In another embodiment, D is

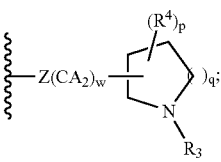

p is 0 and $R^3$ is H or methyl.

In another embodiment, D is

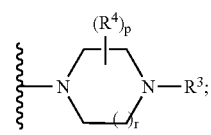

p is 0 and $R^3$ is H or methyl.

In another embodiment, D is

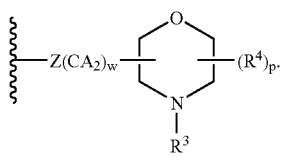

In another embodiment, $R^3$ is H or methyl, w is 1 or 2 and p is 0.

In another embodiment, D is

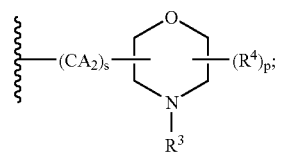

and p is 0.

In another embodiment, $R^3$ is H or methyl, and s is 0 or 1.

In another embodiment, G is hydrogen.

In one embodiment, m is 0 or 1, and $R^6$ is methyl, F or Cl of Formula I.

In another embodiment, each $X^1$, $X^2$, $X^3$, $X^4$ and $X^5$ is $CR^1$, and each $Y^1$, $Y^2$, $Y^3$ and $Y^4$ is $CR^7$ of Formula I.

In another embodiment, each $R^1$ is independently H, methyl, F or Cl, and each $R^7$ is independently H, F or methyl of Formula I.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in S. M. Berge, et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, e.g., chiral alkylating or acylating reagents, followed by cleavage of the chiral auxiliary.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York 1981. Optically active compounds were also be prepared from optically active starting materials.

The invention also encompasses prodrugs of the present compounds, which on administration undergo chemical conversion by metabolic processes before becoming pharmacologically active substances. In general, such prodrugs will be functional derivatives of the compounds of Formula I which are readily convertible in vivo into the required compound of Formula I. Conventional procedures for the selection and preparation of suitable prodrug derivatives are described in Design of Prodrugs, ed. H. Bundgaard, Elsevier, 1985.

Pharmaceutical Compositions

The present invention further provides a pharmaceutical composition comprising a therapeutically effective amount of a compound of Formula I and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of Formula I and a pharmaceutically acceptable carrier. In an embodiment of the present invention the compound utilized in the aforementioned process is one of the specific compounds disclosed in the Experimental Section.

The compounds of this invention are generally utilized as the free substance or as a pharmaceutically acceptable salt thereof. One example is an acid addition salt of a compound having the utility of a free base. When a compound of Formula I contains a free base such salts are prepared in a conventional manner by treating a solution or suspension of a free base of Formula I with a molar equivalent of a pharmaceutically acceptable acid. Representative examples of suitable organic and inorganic acids are described above.

For parenteral administration, solutions of the compounds of Formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of Formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of Formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit.

If a liquid carrier is used, the preparation may be in the form of a syrup, emulsion, soft gelatin capsule or sterile injectable liquid such as an aqueous or non-aqueous liquid suspension or solution.

Treatment of Disorders

As mentioned above, the compounds of Formula I are ligands at the MCH1 receptor. The present invention provides a method of treating a subject suffering from depression and/or anxiety which comprises administering to the subject a therapeutically effective amount of a compound of this invention. This invention further provides a method of treating a subject suffering from major depression and/or anxiety which comprises administering to the subject a therapeutically effective amount of a compound of this invention. This invention also provides a method of treating a subject suffering from obesity which comprises administering to the subject a therapeutically effective amount of a compound of this invention. In an embodiment of this invention, the subject is a human being.

The invention will be better understood from the Experimental Details which follow. However, one skilled in the art will readily appreciate that the specific methods and results discussed therein are merely illustrative of the invention as described more fully in the claims which follow thereafter. Furthermore, the variables depicted in Schemes 1-10 are consistent with the variables recited in the Summary of the Invention. For clarity purposes, the variables $X^1$, $X^2$, $X^3$, $X^4$ and $X^5$ are designated as variable X in the experimental schemes. Moreover, the variables $Y^1$, $Y^2$, $Y^3$ and $Y^4$ are designated as variable Y in the experimental schemes.

In the Experimental Section, standard acronyms are used. Examples of such acronyms include DMF (N,N-Dimethylformamide); DMSO (Dimethylsulfoxide); NBS (N-Bromosuccinimide); HATU (O-(7-Azabenzotriazol-1-yl)-N,N,N',N'-tetramethyluronium hexafluorophosphate); mCPBA (3-chloroperoxybenzoic acid); CbzCl (Benzyl chloroformate); and BOC (tert-butoxycarbonyl). Furthermore in certain instances, the methods of preparing the compounds of the invention are described generally by referring to representative reagents such as bases or solvents. The particular reagent identified is representative but is not inclusive or does not limit the invention in any way. For example, representative bases include but are not limited to $K_2CO_3$, $Et_3N$ or DIPEA (Diisopropylethylamine).

Experimental Section

Methods of Preparing the Compounds of Formula I

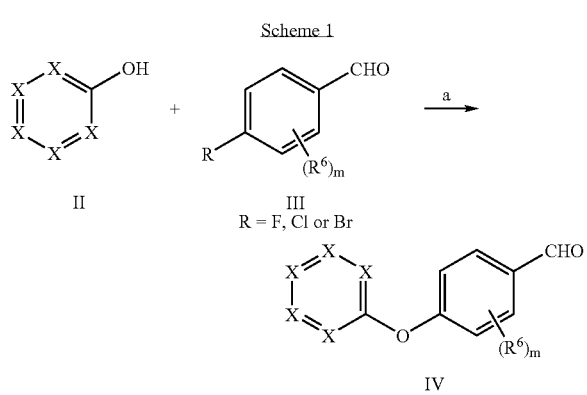

(a) K$_2$CO$_3$/DMF or DMSO/reflux for 6 h or microwave at 250° C. for 5 min.

The 4-(aryloxy)benzaldehydes of Formula IV, are used as starting materials in Scheme 7, and either are available from commercial sources or may be prepared via Ullmann type reaction from the corresponding phenol II and activated aryl halides III in the presence of base under reflux or microwave conditions. Alternatively, 4-(aryloxy)benzaldehydes IV are prepared from the corresponding phenols and aryl halides by means of coupling reactions using palladium or copper catalysis (for references see J. R. Dimmock et al., *J. Med. Chem.* 1996, 39, 3984-3997; Q. Wang et al., *Org. Lett.,* 2003, 5, 2169-2171; J. F. Hartwig et al., *Tetrahedron Lett.* 1997, 38, 8005-8008; S. L. Buchwald et al., *J. Am. Chem. Soc.* 1997, 119, 10539-10540; J. F. Hartwig, *Angew. Chem. Int. Ed.* 1998, 37, 2046-2067; J. S. Sawyer, *Tetrahedron* 2000, 56, 5045; S. V. Ley et al., *Angew. Chem. Int. Ed.* 2003, 42, 5400-5449 and references cited therein).

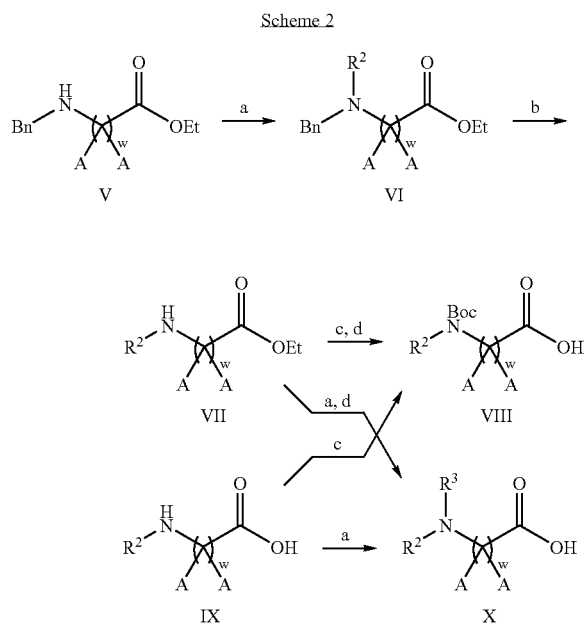

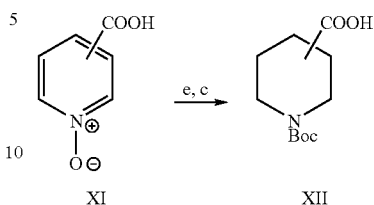

(a) Reductive amination or alkylation.
(b) Deprotection.
(c) Base/Boc$_2$O/DME.
(d) Hydrolysis.
(e) HCOONH$_4$/10% Pd—C/MeOH.

The N-protected primary or secondary amino acids VIII, tertiary amino acids X and N-protected piperidine carboxylic acids XII used as starting materials in Scheme 8 and Scheme 10 are commercially available or prepared according to literature procedures or prepared as outlined in Scheme 2. For example, the N-protected amino acids VIII and tertiary amino acids X are prepared from the corresponding ester V, VI, VII or carboxylic acid IX. The N-protected piperidine carboxylic acids XII may be prepared by reduction of the corresponding substituted pyridine or pyridine N-oxides XI, followed by Boc protection as shown in Scheme 2. (For representative reviews for the preparation of optically active α-amino acids, see: R. M. Williams, In *Synthesis of Optically Active α-Amino Acids*, J. E. Baldwin, Ed.; Organic Chemistry Series, Pergamon Press: Oxford, 1989; R. M. Williams, *Chem. Rev.* 1992, 92, 889; R. O. Duthaler, *Tetrahedron* 1994, 50, 1539; C. Cativiela, *Tetrahedron: Asymmetry* 1998, 9, 3517; C. Cativiela, *Tetrahedron: Asymmetry* 2000, 11, 645; M. J. O'Donnell, *Aldrichimica Acta* 2001, 3, 3-15; *Enzyme Catalysis in Organic Synthesis*; K. Drauz, H. Waldmann, Eds.; Wiley-VCH: Weinheim, 1995; *Stereoselective Biocatalysis*; R. N. Patel, Ed.; Marcel Dekker, New York, 2000; and K. Maruoka, *Chem. Rev.* 2003, 103, 3013-3028. For representative reviews on the preparation of optically active β-amino acids, see: *Enantioselective Synthesis of β-Amino Acids*; E. Juaristi, Wiley-VCH, New York, 1997; M. P. Sibi, *Tetrahedron* 2002, 58, 7991-8035; D. C. Cole, *Tetrahedron* 1994, 50, 9517-9582; E. Juaristi, *Aldrichim. Acta* 1994, 27, 3; G. Cardillo, *Chem. Soc. Rev.* 1996, 25, 117-128; Y. Yamamoto, N. Asgo and W. Tsukada, *Advances in Asymmetric Synthesis* (Ed.: A. Hassner), JAI Press, Stamford, 1998, p. 1. For the preparation of azepane carboxylic acids, see G. I. Georg et al., *Bioorg. Med. Chem. Lett.* 1991, 1, 125-128. For the preparation of piperidine carboxylic acids, see B. Zacharie et al., *J. Org. Chem.* 2001, 66, 5264-5265. For the preparation of pyrrolidine carboxylic acids, see R. Ling et al., *Tetrahedron* 2001, 57, 6579-6588; B. C. J. van Esseveldt et al., *SynLett* 2003, 15, 2354-2358. For the preparation of azetidine carboxylic acids, see S. Hanessian et al., *Bioorg. Med. Chem. Lett.* 1999, 9, 1437-1442; R. A. Miller et al., *Synth. Commun.* 2003, 33, 3347-3353 and references therein).

Scheme 3

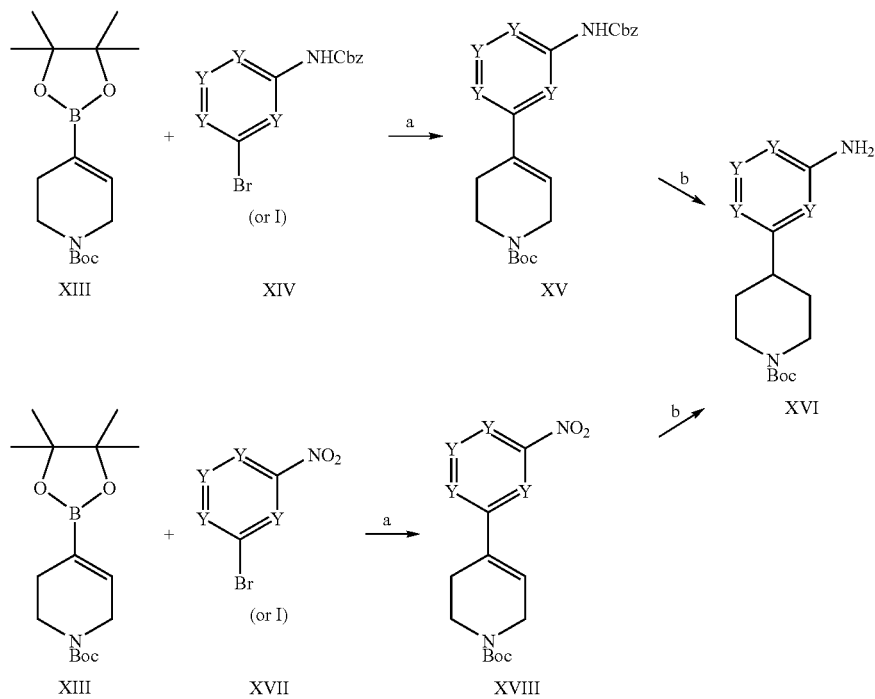

(a) K₂CO₃/PdCl₂dppf/DMF/60-80° C. overnight.
(b) 10% Pd/C/H₂ (50-60 psi)/EtOH/rt 24-72 h.

Intermediate tert-butyl 4-(3-aminoaryl)piperidinecarboxylates of Formula XVI are prepared as outlined in Scheme 3 from tert-butyl 4-(4,4,5,5-tetramethyl-1,3,2-dioxaborolan-2-yl)-1,2,5,6-tetrahydropyridine carboxylate XIII and N—Cbz protected bromo or iodo anilines or amino pyridine XIV via Suzuki coupling followed by simultaneous reduction of the double bond in the tetrahydropyridine ring and removal of the Cbz protecting group by catalytic hydrogenation. Alternatively, tert-butyl 4-(3-aminoaryl)piperidinecarboxylate XVI may be prepared from tert-butyl 4-(4,4,5,5-tetramethyl-1,3,2-dioxaborolan-2-yl)-1,2,5,6-tetrahydropyridine carboxylate XIII and bromo or iodo nitrobenzenes or nitropyridines XVII via Suzuki coupling followed by simultaneous reduction of the double bond and the nitro group by means of catalytic hydrogenation. (Suzuki coupling and hydrogenation reactions are described in the following references: A. Suzuki et al., *Chem. Rev.* 1995, 95, 2457; A. Suzuki, *J. Organomet. Chem.* 1999, 576(1-2), 147-168 and the references cited therein; and P. N. Rylander, *Hydrogenation Methods* (*Best Synthetic Methods Series*), Academic Press, 1990).

tert-Butyl 4-(4,4,5,5-tetramethyl-1,3,2-dioxaborolan-2-yl)-1,2,5,6-tetrahydropyridine carboxylate XIII which is used as starting material in Scheme 3 is prepared according to the procedures described by P. R. Eastwood, *Tetrahedron Lett.* 2000, 41, 3705-3708 and references cited therein.

Scheme 4

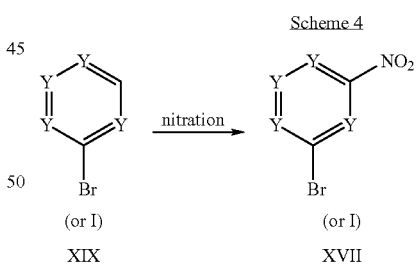

The 3-bromo or 3-iodo nitrobenzenes and nitropyridines XVII which are used as starting material for the synthesis outlined in Scheme 3 are available from commercial sources or may alternatively be prepared from the corresponding bromo or iodo benzenes and pyridines XIX by nitration methods. General information regarding aromatic nitration is described in the following references: J. G. Hoggett, R. B. Moodie, J. R. Penton and K. Schofield, *Nitration and Aromatic Reactivity*, Cambridge University Press, London, 1971; K. Schofield, *Aromatic Nitration*, Cambridge University Press, London, 1980; and G. A. Olah, R. Malhotra and S. C.

Narang, *Nitration: Methods and Mechanism*, (Ed.: H. Feuer), VCH Publishers, New York, 1989.

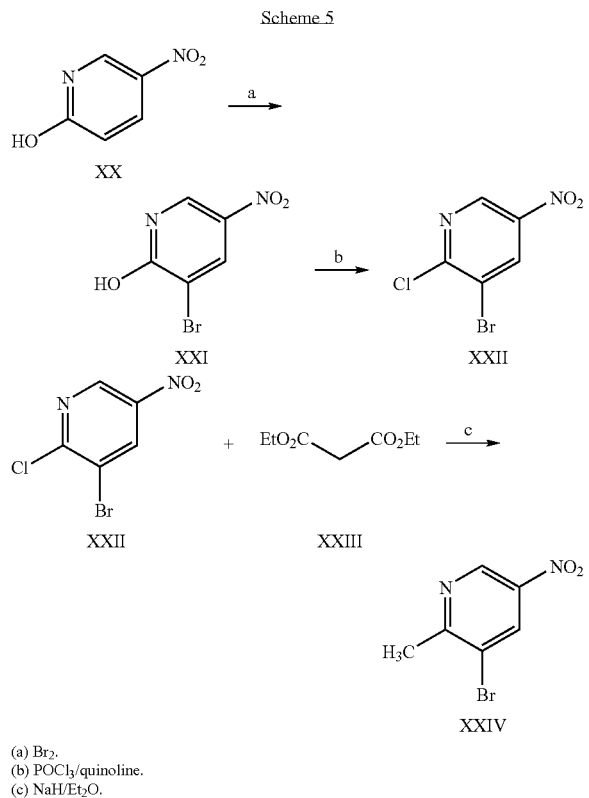

Scheme 5

(a) Br$_2$.
(b) POCl$_3$/quinoline.
(c) NaH/Et$_2$O.

Alternatively, the substituted bromo or iodo nitrobenzenes or nitropyridines XVII may be prepared from commercially available materials via a series of functional group transformation methods known to those skilled in the art. For example, 3-bromo-2-methyl-5-nitropyridine XXIV may be prepared and functionalized from 5-nitropyridin-2-ol XX as shown in Scheme 5.

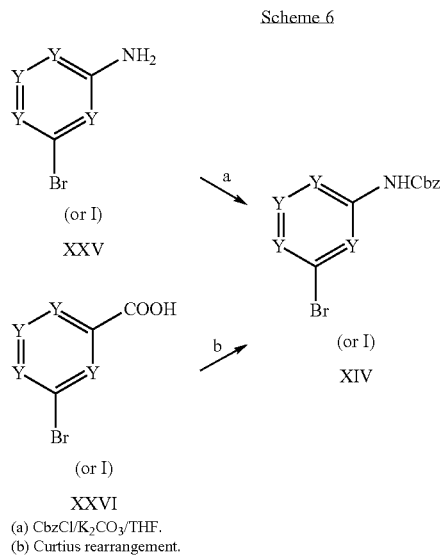

Scheme 6

(a) CbzCl/K$_2$CO$_3$/THF.
(b) Curtius rearrangement.

The N—Cbz protected bromo or iodo anilines and amino pyridine XIV which are used as starting material in the syntheses outlined in Scheme 3 may be prepared by a variety of conditions from commercially available materials. For example, the amino group of commercially available bromo or iodo anilines and amino pyridines XXV may be protected directly by benzyl chloroformate in the presence of base. Alternatively, N—Cbz protected bromo or iodo anilines and amino pyridines XIV may be prepared from the corresponding benzoic acids, isonicotinic acids, nicotinic acids or picolinic acids XXVI using diphenylphosphoryl azide via a Curtius type rearrangement, followed by trapping the isocyanates with benzyl alcohol as described by S. Yamada et al., *Tetrahedron* 1974, 30, 2151-2157.

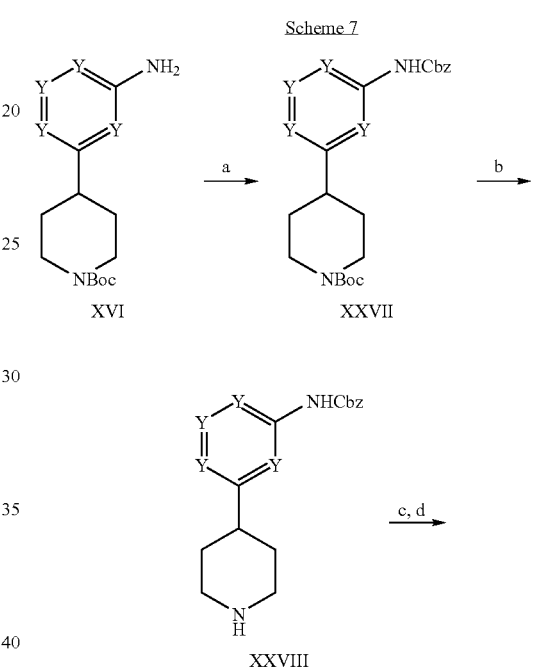

Scheme 7

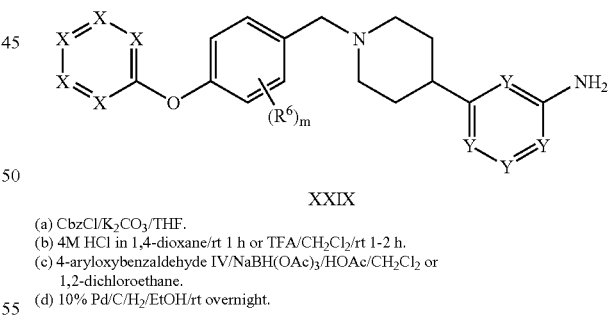

(a) CbzCl/K$_2$CO$_3$/THF.
(b) 4M HCl in 1,4-dioxane/rt 1 h or TFA/CH$_2$Cl$_2$/rt 1-2 h.
(c) 4-aryloxybenzaldehyde IV/NaBH(OAc)$_3$/HOAc/CH$_2$Cl$_2$ or 1,2-dichloroethane.
(d) 10% Pd/C/H$_2$/EtOH/rt overnight.

The key intermediates of Formula XXIX are prepared as outlined in Scheme 7. tert-Butyl 4-(3-aminoaryl)piperidinecarboxylate XVI is acylated with CbzCl in the presence of base to afford tert-butyl 4-{3-[(phenylmethoxy)carbonylamino]aryl}piperidine carboxylate XXVII. The Boc protecting group is removed under acidic conditions to give N-(3-(4-piperidyl)aryl)(phenylmethoxy)carboxamide XXVIII. Reductive amination of piperidine XXVIII with the appropriately substituted 4-(aryloxy)benzaldehyde IV using sodium triacetoxyborohydride followed by removal of the Cbz group by catalytic hydrogenation affords 3-{1-[(4-aryloxyphenyl)methyl]-4-piperidyl}arylamine XXIX.

Scheme 8

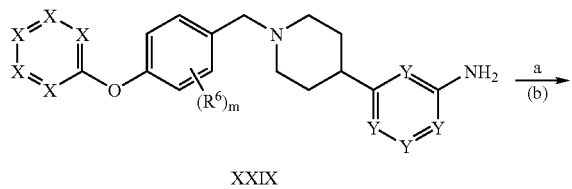

XXIX

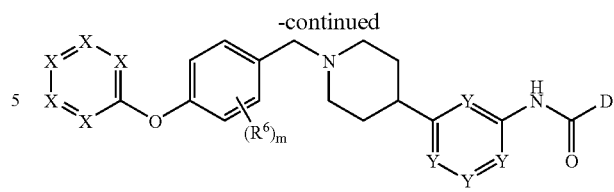

I
(D = D$^1$, D$^2$ or D$^3$)

$$R^3 = H$$
or
$$R^3 = alkyl$$ ⟵ c (a) Amino acid/HATU/DIPEA/DMF/rt.
(b) Deprotection (when R$^3$ = protecting group).
(c) Reductive amination.

Scheme 9

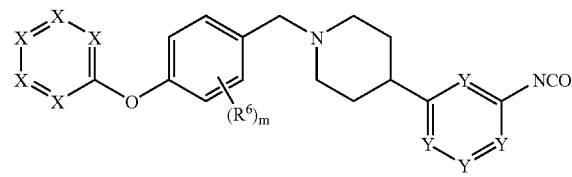

XXX

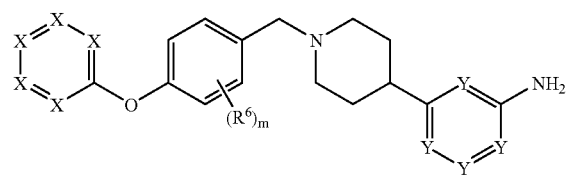

XXIX

I (D = D$^4$, D$^5$, D$^6$, D$^7$ and D$^8$)

$$R^3 = H$$
or
$$R^3 = alkyl$$ ⟶ f

XXXI

R = H or NO$_2$ (a) Triphosgene/Et$_3$N/PhMe 70° C.
(b) Aryl chloroformate/pyridine/CH$_2$Cl$_2$.
(c) Amine or alcohol/base/CH$_2$Cl$_2$.
(d) Amine or alcohol/dioxane/heat or microwave.
(e) Deprotection (when R$^3$ = protecting group).
(f) Reductive amination.

Compounds of the invention of Formula I are prepared as outlined in Scheme 8 (D=D¹, D² or D³) and Scheme 9 (D=D⁴, D⁵, D⁶, D⁷ or D⁸), respectively. 3-{1-[(4-Aryloxyphenyl)methyl]-4-piperidyl}arylamine XXIX is acylated under standard coupling conditions with N-protected amino acids (for primary and secondary amino acids) or amino acids (for tertiary amino acids) to provide the amide derivatives (D=D¹, D² or D³, Scheme 8) followed if necessary, by N-deprotection using standard conditions. The ureas and carbamates of Formula I (D=D⁴, D⁵, D⁶, D⁷ or D⁸) are prepared by the reaction of a diamine or an aminoalcohol (mono-N-protected if necessary) with 3-{1-[(4-aryloxyphenyl)methyl]-4-piperidyl}arylisocyanate XXX or N-[3-(1-{[4-aryloxyphenyl]methyl}(4-piperidyl))aryl](4-nitrophenoxy)carboxamide XXXI, followed by removal of the protecting group (for mono-N-protected diamine or aminoalcohol) to give Formula I wherein D=D⁴, D⁵, D⁶, D⁷ or D⁸.

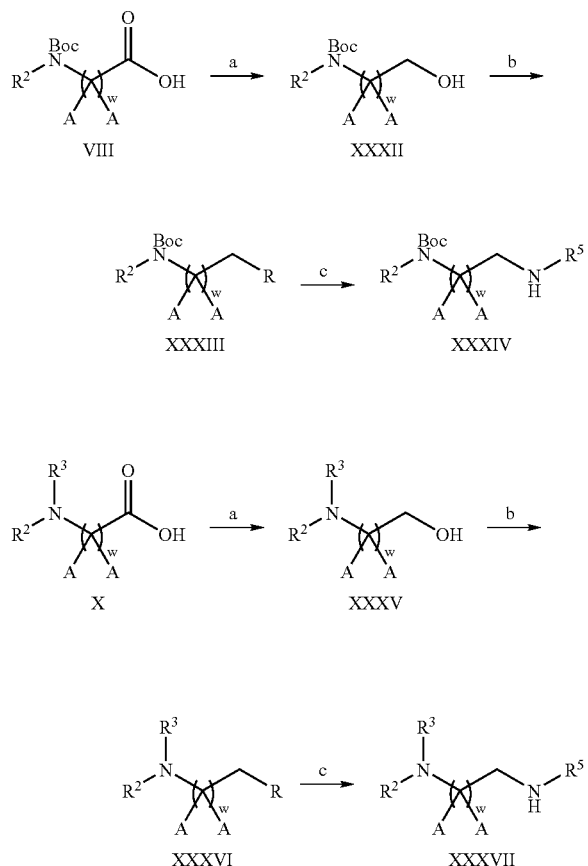

R = leaving group
(OTs, OMs, I, Br or Cl)
(a) Reduction.
(b) Convert hydroxyl group to leaving group.
(c) H₂NR⁵.

The diamines and aminoalcohols, which are used as starting materials for the synthesis outlined in Scheme 9, are available from commercial sources or may alternatively be prepared from the corresponding amino acids by reduction, functional group transformation and nucleophilic substitution with NHR⁵ to give the desired aminoalcohols and diamines such as XXXII, XXXIV, XXXV and XXXVII (Scheme 10). The general information for functional group transformation of the hydroxyl group can be found in the textbook (R. C. Larock, *Comprehensive Organic Transformations*, VCH Publishers, Inc., New York, N.Y., 1999).

3-{1-[(4-aryloxyphenyl)methyl]-4-piperidyl}arylisocyanate XXX is prepared from XXIX by using triphosgene under standard conditions (Scheme 9). The activated phenyl carbamates of Formula XXXI are prepared from XXIX under standard conditions.

Primary and secondary amines of Formula I (R³=H) may be further converted to the tertiary amines (R³=alkyl) via a reductive amination procedure. Any modification of the sequence in the schemes including the use of other protective groups or different conditions for amide, urea, carbamate formation would be apparent to those skilled in the art. The general information for protecting/deprotecting the amino group can be found in the textbook (T. Green and P. G. M. Wuts, *Protective Groups in Organic Synthesis*, John Wiley & Sons, Inc., New York, N.Y., 1999).

General Methods: All reactions were performed under a nitrogen atmosphere and the reagents, neat or in appropriate solvents, were transferred to the reaction vessel via syringe and cannula techniques. Anhydrous solvents were purchased from Aldrich Chemical Company and used as received. The NMR spectra were measured on a Bruker Avance 400 spectrometer or Varian Unity Inova 400 spectrometer in CDCl₃, CD₃OD or D₆-DMSO as the solvent with tetramethylsilane as the internal standard unless otherwise noted. Chemical shifts (δ) are expressed in ppm, coupling constants (J) are expressed in Hz, and splitting patterns are described as follows: s=singlet; d=doublet; t=triplet; q=quartet; quintet; sextet; septet; br=broad; m=multiplet; dd=doublet of doublets; dt=doublet of triplets; td=triplet of doublets; dm=doublet of multiplets; ddd=doublet of doublet of doublets. Unless otherwise noted, mass spectra were obtained using electrospray ionization (ESMS, Micromass Platform II or Quattro Micro) and (M+H)⁺ is reported. Thin-layer chromatography (TLC) was carried out on glass plates pre-coated with silica gel 60 F₂₅₄ (0.25 mm, EM Separations Tech.). Preparative TLC was carried out on glass sheets pre-coated with silica gel GF (2 mm, Analtech). Flash column chromatography was performed on Merck silica gel 60 (230-400 mesh). Melting points (mp) were determined in open capillary tubes on a Mel-Temp apparatus and are uncorrected. Infrared spectra were collected on an Avatar 360 FT-IR instrument. Reverse Phase High Pressure Liquid Chromatography purification was performed using a Genesis HPLC Column (Ref. 16R10985, 100 mm×22.5 mm) containing C18-7 μm, 120 Å silica. Microwave experiments were carried out using a Biotage Emyrs Optimizer™ or Smithcreator. SCX Cartridge: Isolute SCX solid phase extraction cartridge with benzenesulphonic acid based cation exchange sorbent is supplied by Argonaut Technologies. Amino bond elute cartridge: Isolute NH₂ solid phase extraction cartridge with aminopropyl silane covalently bonded to silica is supplied by Argonaut Technologies. Bond elute cartridge: Isolute silica solid phase extraction cartridge with silanol groups on the surface of the silica particle is supplied by Argonaut Technologies. Pall Life Robotic filter funnel: Pall Life Robotic filter funnel (1.2 um Versapor) is supplied by VWR (catalogue number 28143-538).

LCMS methods

| | Method | |
|---|---|---|
| A | B | C |

Mass Spectrometer

| A | B | C |
|---|---|---|
| Platform LCT with electrospray source operating in positive ion mode. Waters 1525 Ic pump running at 1.0 mL/min, HTS PAL autosampler, 100 μL/min split to the ESI source with inline Waters UV2488 Dual Wavelength UV detector at 254 nm and Sedex ELS detection. | Platform LC or ZQ with electrospray source operating in positive and negative ion mode. HP1100 system running at 2.0 mL/min, 200 μL/min split to the ESI source with inline HP1100 DAD detection and SEDEX ELS detection. | Finnigan TSQ700 with electrospray source operating in positive or negative ion mode. HP1050 system running at 2.0 mL/min, 200 μL/min split to the ESI source with inline HP1050 Single Wavelength UV detector at 254 nm. |

Gradient

| Time* | flow** | %A | %B | Time* | flow** | %A | %B | Time* | flow** | %A | %B |
|---|---|---|---|---|---|---|---|---|---|---|---|
| 0.00 | 1.0 | 95 | 5 | 0.00 | 2.0 | 95 | 5 | 0.00 | 2.0 | 95 | 5 |
| 1.00 | 1.0 | 95 | 5 | 0.50 | 2.0 | 95 | 5 | 1.00 | 2.0 | 95 | 5 |
| 15.00 | 1.0 | 5 | 95 | 4.50 | 2.0 | 5 | 95 | 15.00 | 2.0 | 5 | 95 |
| 20.00 | 1.0 | 5 | 95 | 5.50 | 2.0 | 5 | 95 | 17.00 | 2.0 | 5 | 95 |
| 22.00 | 1.0 | 95 | 5 | 6.00 | 2.0 | 95 | 5 | 18.00 | 2.0 | 95 | 5 |
| 25.00 | 1.0 | 95 | 5 | | | | | 20.00 | 2.0 | 95 | 5 |

A: Water (0.1% formic Acid)
B: Acetonitrile (0.1% formic Acid)

A: Water (0.1% formic Acid)
B: Acetonitrile (0.1% formic Acid)

A: Water (0.1% formic Acid)
B: Acetonitrile (0.1% formic Acid)

Column

| A | B | C |
|---|---|---|
| Higgins Clipeus C18, 5 μm, 100 × 3.0 mm | Luna 3μm C18 (2) 30 × 4.6 mm | Higgins Clipeus C18, 5 μm, 100 × 3.0 mm |

*minutes
**mL/minute

Preparation of Intermediates

4-(Aryloxy)benzaldehyde Synthesis:

Intermediate of Formula IV 4-(Aryloxy)benzaldehydes such as 4-(3,4-difluorophenoxy)benzaldehyde and 4-(2,4,5-trifluorophenoxy)benzaldehyde were prepared from the appropriate phenol of Formula II and 4-fluoro benzaldehyde of Formula III according to the procedures described by J. R. Dimmock et al. *J. Med. Chem.* 1996, 39, 3984-3997 and Q. Wang et al. *Org. Lett.*, 2003, 5, 2169-2171.

Amino Acid Synthesis:

2-[(tert-butoxy)-N-propylcarbonylamino]Acetic Acid

Intermediate of Formula VI

Tetramethylammonium triacetoxyborohydride was added to a solution of N-benzylglycine ethyl ester (1.87 mL, 10 mmol), propionaldehyde (1.05 mL, 14 mmol) and acetic acid (0.6 mL) in $CH_2Cl_2$ (20 mL), and the resulting mixture was stirred at room temperature for 18 h. The reaction mixture was partitioned between aqueous $Na_2CO_3$ (2 M, 100 mL) and $CH_2Cl_2$ (3×20 mL) and the combined organic layers were dried over $Na_2SO_4$ and concentrated in vacuo to give ethyl 2-[benzylpropylamino]acetate as a yellow oil (2.25 g, 96% yield). LCMS (method B): 1.52 min, 236.0 $(M+H)^+$.

Intermediate of Formula VII

Ammonium formate (2 g, 31 mmol) was added to a solution of ethyl 2-[benzylpropylamino]acetate (1.05 g, 4.47 mmol) in ethanol (15 mL) and acetic acid (1 mL). The reaction vessel was then carefully flushed with nitrogen gas. Palladium on carbon (10%, 300 mg) was added in one portion, and the resulting mixture was heated at 80° C., under nitrogen for 3 h. The reaction mixture was allowed to cool to room temperature, and filtered through celite filteraid. The filtrate was concentrated in vacuo, (azeotroping with toluene (20 mL) to remove the acetic acid), to give ethyl 2-(propylamino) acetate as a yellow oil (quantitative crude yield). $^1$H NMR ($CDCl_3$) δ 4.14 (q, J=7.1 Hz, 2H), 3.30 (s, 2H), 2.60 (dd, J=7.4 Hz, 2H), 1.50 (m, 2H), 1.26 (t, J=7.2 Hz, 3H), 0.89 (t, J=7.4 Hz, 3H).

Intermediate of Formula VIII

Di-tert-butyl dicarbonate (1.2 g, 6.9 mmol) was dissolved in dimethoxyethane (10 mL) and this solution was added to a stirred solution of ethyl 2-(propylamino)acetate in aqueous NaOH (1 M, 10 mL). Stirring was continued for 2.5 h, then hydrochloric acid (2 N, 30 mL) was added and the mixture was extracted with ethyl acetate (2×20 mL). The organic layers were dried over $Na_2SO_4$ and concentrated in vacuo to give the intermediate ester as a yellow oil. The yellow oil was dissolved in ethanol (10 mL) and LiOH (1 M, 20 mL) was added and the resulting solution was stirred for 1 h. The mixture was acidified with hydrochloric acid (2 N) and extracted with ethyl acetate (2×20 mL). The combined organic layers were dried over $Na_2SO_4$ and concentrated in vacuo to give the title compound 2-[(tert-butoxy)-N-propylcarbonylamino]acetic acid as a pink oil which crystallized on standing (398 mg, 36% yield from ethyl 2-[benzylpropylamino]acetate). $^1$H NMR ($CDCl_3$), δ 3.87 (m, 2H), 3.18 (m, 2H), 1.46 (s, 9H), 1.35 (m, 2H), 0.82 (t, J=7.4 Hz, 3H).

The following compound of Formula VIII was prepared analogously:

2-[(tert-butoxy)-N-ethylcarbonylamino]acetic acid

A solution of di-tert-butyl dicarbonate (2.18 g, 12.5 mmol) in dimethoxyethane (30 mL) was added to a stirred solution of 2-(ethylamino)acetic acid in $Na_2CO_3$ (1.04 g, 10 mmol in water, 30 mL). Stirring was continued for 4 h, then the reaction mixture was acidified with hydrochloric acid (1 N, 30 mL) and extracted with ethyl acetate (3×30 mL). The organic layers were dried over $Na_2SO_4$ and concentrated in vacuo to give 2-[(tert-butoxy)-N-ethylcarbonylamino]acetic acid as a colorless oil in quantitative yield. $^1$H NMR (CDCl$_3$), δ 3.95 (m, 2H), 3.30 (m, 2H), 1.45 (m, 9H), 1.12 (t, J=7.2 Hz, 3H).

tert-Butyl 4-(3-aminoaryl)piperidinecarboxylate synthesis:

Intermediate of Formula XIII tert-Butyl 4-(4,4,5,5-tetramethyl-1,3,2-dioxaborolan-2-yl)-1,2,5,6-tetrahydropyridine carboxylate was prepared according to the procedures described by P. R. Eastwood, *Tetrahedron Lett.* 2000, 41, 19, 3705-3708 and references cited therein.

Intermediate of Formula XVII

1-Bromo-2,4-difluoro-5-nitrobenzene: To a 0° C. mixture of 1-bromo-2,4-difluorobenzene (20.0 g, 11.7 mL, 0.100 mol) and $H_2SO_4$ (76.8 mL) was added $HNO_3$ (68.0 mL) over 45 min at such a rate that the internal temperature was <7° C. The resulting mixture was stirred for 1 h at 0° C., poured into ice water (400 mL), stirred vigorously for 2-3 min and extracted with $CH_2Cl_2$ (400 mL). The organic layers were washed with brine (1×500 mL), dried over $Na_2SO_4$, filtered and evaporated to give the product as a yellow oil (23.5 g, 95% yield). $^1$H NMR (CDCl$_3$) δ 8.39 (t, J=7.2 Hz, 1H), 7.14 (ddd, J=0.3, 7.8, 9.9 Hz, 1H).

The following intermediates of Formula XVII were prepared analogously:

2-Bromo-5-fluoro-4-nitro toluene: To a mixture of nitronium tetrafluoroborate (11.6 g, 87.0 mmol) and $CH_2Cl_2$ (60.0 mL) was added 2-bromo-5-fluoro toluene (15.0 g, 10.0 mL, 79.0 mmol) over 5 minutes. After refluxing for 4.5 h, the mixture was cooled to room temperature and poured into ice water (150 mL). The mixture was extracted with $CH_2Cl_2$ (3×50 mL). The combined organic layers were washed with brine (100 mL), dried over $Na_2SO_4$, filtered and concentrated to give 18.3 g of crude product. The crude product was treated with hexane and cooled to −70° C. then the hexane was decanted away from the resulting solid to give the desired product as a semi-solid (9.77 g, 53% yield). The mother liquors were evaporated and purified by column chromatography (silica gel, 2% EtOAc in Hexane) to give 1.0 g of the desired product. $^1$H NMR (CDCl$_3$) δ 8.26 (d, J=6.9 Hz, 1H), 7.20 (d, J=11.7 Hz, 1H), 2.48 (s, 3H).

1-Bromo-3-nitro-2,4,6-trifluorobenzene: To a cooled (1.3° C.) mixture of 1-bromo-2,4,6-trifluoroben (30.0 g, 142 mmol) and $H_2SO_4$ (115 mL) was added $HNO_3$ (68%, 102 mL) over 1.5 h at such a rate that the internal temperature was <8° C. After stirring at 0° C. for 2 h, the resulting mixture were poured into ice water (1850 mL), stirred vigorously for 30 min and extracted with $CH_2Cl_2$ (3×600 mL). The combined organic layers were washed with water (2×600 mL), dried over $MgSO_4$, filtered and concentrated to give the desired product as a clear yellow oil (35.0 g, 99% yield). $^1$H NMR (CDCl$_3$) δ 7.01 (ddd, J=2.4, 7.8, 9.3 Hz, 1H); $^{19}$F NMR (CDCl$_3$) δ −116.20 to −116.10, −107.73 to −107.71, −93.80 to −93.70.

3-Bromo-2-methyl-5-nitropyridine:

Intermediate of Formula XXI

Step 1: A mixture of 2-hydroxy-5-nitropyridine (50 g; 0.358 mol) and water (7 L) were warmed to 40° C. and bromine (21 mL, 0.393 mol) was added dropwise over ~20 min. After stirring at 40° C. for 2.5 h, the mixture was cooled to 10° C. and the crude product was isolated by filtration. The solid was washed with water and dried in vacuo to give 3-bromo-2-hydroxy-5-nitropyridine as a solid (70 g, 90% yield). mp 212-214° C. (with decomposition); $^1$H NMR (CD$_3$OD) δ 8.66 (d, J=2.9 Hz, 1H), 8.64 (d, J=2.9 Hz, 1H).

Intermediate of Formula XXII

Step 2: To a cooled (0-5° C.) mixture of 3-bromo-2-hydroxy-5-nitropyridine (47 g, 0.214 mol) and quinoline (13.7 g, 0.107 mol) was added POCl$_3$ (26 mL, 0.278 mol) dropwise over ~10 min (the mixture was difficult to stir initially but became less viscous as the reaction progressed and the mixture warmed). After stirring at 120° C. for 3.5 h, the mixture was cooled to 100° C. and water (90 mL) was added. The resulting mixture was stirred vigorously while cooling to 0-5° C. The product was collected by filtration, washed with water and dried in vacuo at 45° C. to give 42 g of 3-bromo-2-chloro-5-nitropyridine (82% yield). $^1$H NMR (CD$_3$OD) δ 9.19 (d, J=2.4 Hz, 1H), 8.93 (d, J=2.4 Hz, 1H).

Intermediate of Formula XVII or XXIV

Step 3: To a cooled (15° C.) solution of diethyl malonate (8.8 mL, 58 mmol) in diethyl ether (110 mL) was added NaH (as a 60% dispersion in oil, 2.32 g, 58 mmol) over 5 min and 3-bromo-2-chloro-5-nitropyridine (12.5 g, 52.6 mmol) was added in four portions over ~15 min (an exotherm to 26° C. was observed), followed by removal of diethyl ether in vacuo to give a red oil. After stirring the resulting red oil at 114° C. for 1 h 15 min, $H_2SO_4$ (6M, 67 mL) was added. The resulting mixture was heated at reflux for 8 h then cooled to 0° C. and the pH value was adjusted to 7 with 25% KOH aqueous solution (135 mL). The resulting mixture was stirred in an ice bath for 25 min and the crude product was collected and washed with water (50 mL) by filtration. The crude product was stirred in $CH_2Cl_2$ (350 mL) for 30 min and the impurity was removed by filtration. The organic layer was dried over $Na_2SO_4$, filtered and concentrated to give 11.1 g of the impure product as red oil. The red oil was dissolved in $CH_2Cl_2$ (100 mL) and hexanes (200 mL). The resulting mixture was filtered and the organic portion was concentrated to give 9.3 g of 3-bromo-2-methyl-5-nitropyridine as an orange crystalline solid (81% yield). $^1$H NMR (CDCl$_3$) δ 9.25 (d, J=2.3 Hz, 1H), 8.61 (d, J=2.3 Hz, 1H), 2.80 (s, 3H).

Intermediate of Formula XIV

Benzyl 5-bromo-3-pyridinyl carbamate: To a suspension of 5-bromonicotinic acid (20.0 g, 99.0 mmol) in toluene (200 mL) was added diphenylphosphoryl azide (25.6 mL, 118.8 mmol) and Et$_3$N (16.6 mL, 118.8 mmol). After stirring at room temperature for 30 min, benzyl alcohol (15.4 mL, 148.5 mmol) was added. The mixture was stirred at room temperature for 1 h then refluxed overnight. After cooling to room temperature, the reaction mixture was washed with H$_2$O, saturated aqueous NaHCO$_3$ and brine, dried over MgSO$_4$ and concentrated. Purification by flash chromatography (15-50% EtOAc in Hexane) provided 22.2 g (72.5 mmol, 73% yield) of benzyl 5-bromo-3-pyridinylcarbamate: $^1$H NMR (CDCl$_3$) δ 8.39-8.32 (m, 2 H), 8.29 (s, 1 H), 7.45-7.32 (m, 5 H), 6.94 (s, 1 H), 5.22 (s, 2 H); ESMS m/e: 307.0 (M+H)$^+$.

Intermediate of Formula XVI tert-Butyl 4-(3-aminophenyl)piperidinecarboxylate, tert-butyl 4-(3-amino-4-fluorophenyl) piperidinecarboxylate, tert-butyl 4-(3-amino-4,6-difluorophenyl)piperidine carboxylate were prepared according to the procedures described by M. R. Marzabadi et al. in PCT WO 2004/005257 A1 (pp.48-82).

The following intermediates of Formula XVI were prepared analogously:

tert-Butyl 4-(3-amino-6-methylphenyl)piperidinecarboxylate $^1$H NMR (CDCl$_3$) δ 6.93 (d, J=8.1 Hz, 1H), 6.53 (d, J=2.4 Hz, 1H), 6.47 (dd, J=2.4, 8.1 Hz, 1H), 4.30-4.18 (m, 2H), 3.53 (br s, 2H), 2.86-2.51 (m, 3H), 2.23 (s, 3H), 1.77-1.68 (m, 2H), 1.50-1.63 (m, 2H), 1.49 (s, 9H).

tert-Butyl 4-(3-amino-6-fluorophenyl)piperidinecarboxylate $^1$H NMR (CDCl$_3$) δ 6.85-6.76 (m, 1H), 6.51-6.44 (m, 2H), 4.30-4.15 (m, 2H), 3.51 (br s, 2H), 2.98-2.73 (m, 3H), 1.82-1.73 (m, 2H), 1.66-1.50 (m, 2H), 1.48 (s, 9H).

tert-Butyl 4-(3-amino-4-fluoro-6-methylphenyl)piperidinecarboxylate $^1$H NMR (CDCl$_3$) δ 6.77 (d, J=12.0 Hz, 1H), 6.60 (d, J=9.0 Hz, 1H), 4.32-4.16 (m, 2H), 3.86-3.52 (br, 2H), 2.86-2.67 (m, 3H), 2.22 (s, 3H), 1.69 (m, 2H), 1.60-1.43 (m, 11H).

tert-Butyl 4-(3-amino-2,4,6-trifluorophenyl)piperidinecarboxylate $^1$H NMR (CDCl$_3$) δ 6.67-6.54 (m, 1H), 4.32-4.15 (m, 2H), 3.60-3.48 (m, 2H), 3.10-2.97 (m, 1H), 2.84-2.68 (m, 2H), 2.06-1.88 (m, 2H), 1.70-1.60 (m, 2H), 1.46 (s, 9H).

tert-Butyl 4-(5-amino-3-pyridyl)piperidinecarboxylate $^1$H NMR (CDCl$_3$) δ 8.01-7.95 (m, 1 H), 7.89 (s, 1H), 6.83 (s, 1H), 4.39-4.09 (br, 2H), 3.90-3.50 (br, 2H), 2.88-2.68 (m, 2H), 2.67-2.52 (m, 1H), 1.88-1.71 (m, 2H), 1.68-1.49 (m, 2H), 1.48 (s, 9H); ESMS m/e: 278.3 (M+H)$^+$.

tert-Butyl 4-(5-amino-2-methyl-3-pyridyl)piperidinecarboxylate $^1$H NMR (CDCl$_3$) δ 7.87 (d, J=2.7 Hz, 1H), 6.80 (d, J=2.7 Hz, 1H), 4.33-4.17 (m, 2H), 3.57-3.50 (br, 2H), 2.88-2.70 (m, 3H), 2.46 (s, 3H), 1.79-1.70 (m, 2H), 1.61-1.43 (m, 11H).

3-{1-[(4-aryloxyphenyl)methyl]-4-piperidyl}phenylamine synthesis:

4-Methyl-3-(1-{[4-(2,4,5-trifluorophenoxy)phenyl]methyl}(4-piperidyl))phenylamine was synthesized according to Scheme 7 from the intermediate of Formula XVI:

Intermediate of Formula XXVII
Step 1: Benzyl chloroformate (95%, 4.52 mL, 30.06 mmol) was added dropwise to a stirred mixture of tert-butyl 4-(3-amino-6-methylphenyl)piperidinecarboxylate (6.99 g, 24.05 mmol) and K$_2$CO$_3$ (3.66 g, 26.45 mmol) in tetrahydrofuran (350 mL). Stirring was continued under nitrogen for 18 h, then CH$_2$Cl$_2$ was added and the resulting mixture was washed with NaHCO$_3$ solution (saturated), followed by water, then dried over Na$_2$SO$_4$ and concentrated in vacuo to give an oil. Flash column chromatography (silica gel 60) eluting with cyclohexane:ethyl acetate (87:13) provided tert-butyl 4-{2-methyl-5-[(phenylmethoxy)carbonylamino]phenyl}piperidinecarboxylate (7.9 g, 77% yield) as a white foam. LCMS (method B): 4.36 min, 425.0 (M+H)$^+$.

Intermediate of Formula XXVIII
Step 2: tert-butyl 4-{2-methyl-5-[(phenylmethoxy)carbonylamino]phenyl}piperidine carboxylate (7.5 g, 17.6 mmol) was dissolved in CH$_2$Cl$_2$ (120 mL) and hydrogen chloride solution (4 M in dioxane, 52 mL) was added and stirring was continued for 1 h. The mixture was concentrated in vacuo and redissolved in CH$_2$Cl$_2$. An aqueous Na$_2$CO$_3$ solution (1 M) was added and the biphasic mixture was stirred for 20 min, then separated. The organic layer was further washed with water, then dried over Na$_2$SO$_4$ and concentrated in vacuo to provide N-(4-methyl-3-(4-piperidyl)phenyl)(phenylmethoxy)carboxamide (5.61 g, 98% yield) as a white solid. LCMS (method B): 2.22 min, 326.0 (M+H)$^+$.

Step 3: N-(4-methyl-3-(4-piperidyl)phenyl)(phenylmethoxy) carboxamide (3.19 g, 9.81 mmol) and 4-(2,4,5-trifluorophenoxy)benzaldehyde (2.48 g, 9.81 mmol) were dissolved in dichloroethane (110 mL) and acetic acid (1.12 mL, 13.62 mmol), and sodium triacetoxyborohydride (4.2 g, 13.5 mmol) was added portionwise. Stirring was continued under nitrogen at room temperature for 18 h, then saturated aqueous NaHCO$_3$ solution and CH$_2$Cl$_2$ was added. The mixture was separated, and the organic layer was washed with water, dried over Na$_2$SO$_4$ and concentrated in vacuo. Flash column chromatography (silica gel 60) eluting with cyclohexane:ethyl acetate (85:15 then 7:3) provided N-[4-methyl-3-(1-{[4-(2,4,5-trifluorophenoxy)phenyl]methyl}(4-piperidyl))phenyl] (phenylmethoxy) carboxamide (4.89 g, 88% yield) as a white foam. LCMS (method B): 2.93 min, 562.0 (M+H)$^+$.

Intermediate of Formula XXIX
Step 4: N-[4-methyl-3-(1-{[4-(2,4,5-trifluorophenoxy)phenyl]methyl}(4-piperidyl))phenyl](phenylmethoxy)carboxamide (4.88 g, 8.68 mmol) was dissolved in ethanol (150 mL) and hydrogenated over palladium on carbon (10%, 980 mg) for 2.5 h. The reaction mixture was filtered through celite filter aid, washing with ethanol and the filtrate was concentrated in vacuo. Flash column chromatography (silica gel 60) eluting with cyclohexane:ethyl acetate (1:1 then 1:4) provided 4-methyl-3-(1-{[4-(2,4,5-trifluorophenoxy)phenyl]methyl}(4-piperidyl))phenylamine (3.71 g, 100% yield). LCMS (method B): 2.14 min, 427.0 (M+H)$^+$; $^1$H NMR (400 MHz, CD$_3$OD) δ 7.63 (d, 2H, J=7.2 Hz), 7.41-7.33 (m, 2H), 7.27-7.23 (m, 2H), 7.15 (d, 1H, J=8.0 Hz), 7.09 (d, 2H, J=8.0 Hz), 4.36 (s, 2H), 3.61 (d, 2H, J=12.0 Hz), 3.22 (t, 3H, J=12.0 Hz), 2.42 (s, 3H), 2.15-2.02 (m, 4H).

The following intermediates were prepared analogously:

3-(1-{[4-(3,4-difluorophenoxy)phenyl]methyl}(4-piperidyl))-4-methylphenylamine: LCMS (method A): 6.84 min, 409.0 (M+H)$^+$.

5-(1-{[4-(3,4-difluorophenoxy)phenyl]methyl}(4-piperidyl))-2-fluoro-4-methylphenylamine: LCMS (method A): 8.45 min, 427.2 (M+H)$^+$.

5-(1-{[4-(3,4-difluorophenoxy)phenyl]methyl}-4-piperidyl)-3-pyridylamine: LCMS (method A): 6.75 min, 396.2 (M+H)$^+$.

6-methyl-5-(1-{[4-(2,4,5-trifluorophenoxy)phenyl]methyl}(4-piperidyl))-3-pyridylamine: LCMS (method A): 5.87 min, 428.2 (M+H)$^+$.

3-(1-{[4-(3,4-difluorophenoxy)phenyl]methyl}(4-piperidyl))-2,4,6-trifluorophenylamine: LCMS (method A): 8.65 min, 449.2 (M+H)$^+$.

5-(1-{[4-(3,4-difluorophenoxy)phenyl]methyl}(4-piperidyl))-2,4-difluorophenylamine: LCMS (method A): 8.97 min, 431.3 (M+H)$^+$.

2-fluoro-4-methyl-5-(1-{[4-(2,4,5-trifluorophenoxy)phenyl]methyl}(4-piperidyl))phenylamine: LCMS (method A): 8.45 min, 445.2 (M+H)$^+$.

2,4-difluoro-5-(1-{[4-(2,4,5-trifluorophenoxy)phenyl]methyl}(4-piperidyl))phenylamine: LCMS (method A): 8.97 min, 449.2 (M+H)$^+$.

5-(1-{[4-(2,4,5-trifluorophenoxy)phenyl]methyl}4-piperidyl)-3-pyridylamine: LCMS (method A): 6.70 min, 414.2 (M+H)$^+$.

2,4,6-trifluoro-3-(1-{[4-(2,4,5-trifluorophenoxy)phenyl]methyl}(4-piperidyl))phenylamine: LCMS (method A): 8.62 min, 467.2 (M+H)$^+$.

5-(1-{[4-(3,4-difluorophenoxy)phenyl]methyl}(4-piperidyl))-6-methyl-3-pyridylamine: LCMS (method A): 5.85 min, 410.3 (M+H)$^+$.

EXAMPLES

Example 1a 2-(methylamino)-N-[4-methyl-3-(1-{[4-(2,4,5-trifluorophenoxy)phenyl]methyl}(4-piperidyl))phenyl]acetamide dihydrochloride:

To a stirred solution of 4-methyl-3-(1-{[4-(2,4,5-trifluorophenoxy)phenyl]methyl}(4-piperidyl))phenylamine (271 mg, 0.64 mmol) in dimethylformamide (15 mL) was added 2-[(tert-butoxy)-N-methylcarbonylamino]acetic acid (361 mg, 1.91 mmol) followed by O-(7-azabenzotriazol-1-yl)-N,N,N',N'-tetramethyluronium hexafluorophosphate (HATU, 728 mg, 1.91 mmol) and diisopropylethylamine (328 mg, 2.54 mmol). After stirring at room temperature for 21 h, the reaction mixture was partitioned between $CH_2Cl_2$ (30 mL) and saturated aqueous $NaHCO_3$ (30 mL). The organic layer was washed with water (3×30 mL) and brine (30 mL), dried over $MgSO_4$ and concentrated in vacuo provided the crude product. Purification on silica gel (silica gel 60, 40 mL) eluting with $CH_2Cl_2$ then 3% methanol in $CH_2Cl_2$ to give 2-[(tert-butoxy)-N-methylcarbonylamino]-N-[4-methyl-3-(1-{[4-(2,4,5-trifluorophenoxy)phenyl]methyl}(4-piperidyl))phenyl]acetamide (345 mg, 0.58 mmol, 90% yield) as a white solid. LCMS (method B): 2.81 min, 598.3 (M+H)$^+$.

2-[(tert-butoxy)-N-methylcarbonylamino]-N-[4-methyl-3-(1-{[4-(2,4,5-trifluorophenoxy) phenyl]methyl}(4-piperidyl))phenyl]acetamide was dissolved in $CH_2Cl_2$ (15 mL) and trifluoroacetic acid (5 mL) was added dropwise to the stirred solution. Stirring was continued for 30 minutes then the reaction mixture was concentrated in vacuo to give a gum. This was partitioned between $CH_2Cl_2$ (2×30 mL) and saturated aqueous $NaHCO_3$ (30 mL). The combined organic layers were dried over $MgSO_4$ and concentrated in vacuo to give the free base. This was dissolved in methanolic hydrogen chloride (1.6 M, 5 mL), and concentrated in vacuo to yield 2-(methylamino)-N-[4-methyl-3-(1-{[4-(2,4,5-trifluorophenoxy)phenyl]methyl}(4-piperidyl))phenyl]acetamide dihydrochloride (292 mg, 88% yield) as a white solid. LCMS (method A): 7.35 min, 498.3 (M+H)$^+$; $^1$H NMR ($D_6$-DMSO) δ 11.20 (br s, 1H), 10.68 (s, 1H), 9.03 (m, 2H), 7.84 (td, J=10.7, 7.7 Hz, 1H), 7.67 (m, 2H), 7.59 (dt, J=11.0, 8.0 Hz, 1H), 7.40 (m, 2H), 7.13 (d, J=8.5 Hz, 1H), 7.09 (m, 2H), 4.27 (d, J=5.1 Hz, 2H), 3.90 (t, J=5.7 Hz, 2H), 3.39 (d, J=11.8 Hz, 2H), 3.06 (m, 2H), 2.95 (m, 1H), 2.61 (t, J=5.4 Hz, 3H), 2.26 (s, 3H), 2.04 (m, 2H,), 1.86 (d, J=13.4 Hz, 2H).

The following compounds were prepared analogously:

Example 1b

N-[5-(1-{[4-(3,4-difluorophenoxy)phenyl]methyl}(4-piperidyl))-2,4-difluorophenyl]-4-piperidylcarboxamide dihydrochloride ESMS m/e: 542.3 (M+H)$^+$.

Example 1c (1-methyl(4-piperidyl))-N-[4-methyl-3-(1-{[4-(2,4,5-trifluorophenoxy)phenyl]methyl}(4-piperidyl))phenyl]carboxamide dihydrochloride LCMS (method C): 4.94 min, 552.0 (M+H)$^+$.

Example 1d

N-[4-methyl-3-(1-{[4-(2,4,5-trifluorophenoxy)phenyl]methyl}(4-piperidyl))phenyl]-4-piperidylcarboxamide dihydrochloride LCMS (method A): 6.65 min, 538.1 (M+H)$^+$.

Example 1e 2-(dimethylamino)-N-[4-methyl-3-(1-{[4-(2,4,5-trifluorophenoxy)phenyl]methyl}(4-piperidyl))phenyl]acetamide dihydrochloride LCMS (method C): 5.59 min, 512.0 (M+H)$^+$.

Example 1f 2-((2S)pyrrolidin-2-yl)-N-[4-methyl-3-(1-{[4-(2,4,5-trifluorophenoxy)phenyl]methyl}(4-piperidyl))phenyl]acetamide dihydrochloride LCMS (method C): 4.71 min, 538.0 (M+H)$^+$.

Example 1g

N-[4-methyl-3-(1-{[4-(2,4,5-trifluorophenoxy)phenyl]methyl}(4-piperidyl))phenyl]-3-piperidylpropanamide dihydrochloride LCMS (method A): 6.60 min, 566.2 (M+H)$^+$.

Example 1h 3-(dimethylamino)-N-[4-methyl-3-(1-{[4-(2,4,5-trifluorophenoxy)phenyl]methyl}(4-piperidyl))phenyl]propanamide dihydrochloride LCMS (method A): 6.75 min, 526.2 (M+H)$^+$.

Example 1i

N-[4-methyl-3-(1-{[4-(2,4,5-trifluorophenoxy)phenyl]methyl}(4-piperidyl))phenyl]-2-morpholin-4-ylacetamide dihydrochloride LCMS (method A): 6.88 min, 554.2 (M+H)$^+$.

Example 1j (1-methyl(2-piperidyl))-N-[4-methyl-3-(1-{[4-(2,4,5-trifluorophenoxy)phenyl]methyl}(4-piperidyl))phenyl]carboxamide dihydrochloride LCMS (method A): 6.97 min, 552.2 (M+H)$^+$.

Example 1k

N-[4-methyl-3-(1-{[4-(2,4,5-trifluorophenoxy)phenyl]methyl}(4-piperidyl))phenyl]-3-morpholin-4-ylpropanamide dihydrochloride LCMS (method A): 6.85 min, 568.2 (M+H)$^+$.

Example 1l ((2R)pyrrolidin-2-yl)-N-[4-methyl-3-(1-{[4-(2,4,5-trifluorophenoxy)phenyl]methyl}(4-piperidyl))phenyl]carboxamide dihydrochloride LCMS (method C): 4.54 min, 524.0 (M+H)$^+$.

Example 1m ((2S)-1-methylpyrrolidin-2-yl)-N-[4-methyl-3-(1-{[4-(2,4,5-trifluorophenoxy)phenyl]methyl}(4-piperidyl))phenyl]carboxamide dihydrochloride LCMS (method C): 4.57 min, 538.0 (M+H)$^+$.

Example 1n

N-[4-methyl-3-(1-{[4-(2,4,5-trifluorophenoxy)phenyl]methyl}(4-piperidyl))phenyl]-2-piperidylcarboxamide dihydrochloride LCMS (method A): 6.66 min, 538.1 (M+H)$^+$.

Example 1o (2S)-3-methyl-2-(methylamino)-N-[4-methyl-3-(1-{[4-(2,4,5-trifluorophenoxy)phenyl]methyl}(4-piperidyl))phenyl]butanamide dihydrochloride LCMS (method C): 4.53 min, 540.0 (M+H)$^+$.

Example 1p

N-[4-methyl-3-(1-{[4-(2,4,5-trifluorophenoxy)phenyl]methyl}(4-piperidyl))phenyl]-3-piperidylcarboxamide dihydrochloride LCMS (method C): 4.49 min, 538.0 (M+H)$^+$.

Example 1q (2S)-2-(methylamino)-N-[4-methyl-3-(1-{[4-(2,4,5-trifluorophenoxy)phenyl]methyl}(4-piperidyl))phenyl]propanamide dihydrochloride LCMS (method A): 6.67 min, 512.4 (M+H)$^+$.

Example 1r

N-[4-methyl-3-(1-{[4-(2,4,5-trifluorophenoxy)phenyl]methyl}(4-piperidyl))phenyl]-2-(4-piperidyl)acetamide dihydrochloride LCMS (method A): 6.86 min, 552.2 (M+H)$^+$.

Example 1s ((2S)pyrrolidin-2-yl)-N-[4-methyl-3-(1-{[4-(2,4,5-trifluorophenoxy)phenyl]methyl}(4-piperidyl))phenyl]carboxamide dihydrochloride LCMS (method A): 6.75 min, 524.1 (M+H)$^+$.

Example 1t

N-[3-(1-{[4-(3,4-difluorophenoxy)phenyl]methyl}(4-piperidyl))-4-methylphenyl](1-methyl(4-piperidyl))carboxamide dihydrochloride LCMS (method A): 8.47 min, 534.1 (M+H)$^+$.

Example 1u

N-[3-(1-{[4-(3,4-difluorophenoxy)phenyl]methyl}(4-piperidyl))-4-methylphenyl]-4-piperidylcarboxamide dihydrochloride LCMS (method A): 8.19 min, 520.1 (M+H)$^+$.

Example 1v 2-(ethylamino)-N-[4-methyl-3-(1-{[4-(2,4,5-trifluorophenoxy)phenyl]methyl}(4-piperidyl))phenyl]acetamide dihydrochloride LCMS (method A): 8.31 min, 512.1 (M+H)$^+$.

Example 1w

N-[4-methyl-3-(1-{[4-(2,4,5-trifluorophenoxy)phenyl]methyl}(4-piperidyl))phenyl]-2-(propylamino)acetamide dihydrochloride LCMS (method C): 4.98 min, 526.0 (M+H)$^+$.

Example 2a (1-methyl(3-piperidyl))-N-[4-methyl-3-(1-{[4-(2,4,5-trifluorophenoxy)phenyl]methyl}(4-piperidyl))phenyl]carboxamide dihydrochloride A mixture of 4-methyl-3-(1-{[4-(2,4,5-trifluorophenoxy)phenyl]methyl}(4-piperidyl)) phenylamine (70 mg, 0.164 mmol), piperidine-1,3-dicarboxylic acid 1-tert-butyl ester (113 mg, 0.492 mmol), O-(7-azabenzotriazol-1-yl)-N,N,N',N'-tetramethyluronium hexafluorophosphate (HATU, 188 mg, 0.492 mmol) and diisopropylethylamine (85 mg, 0.657 mmol) in dimethylformamide (5 mL) was stirred at room temperature for 18 h. The mixture was partitioned between water (20 mL) and CH$_2$Cl$_2$ (2×20 mL). The combined organic layers were washed with water (2×20 mL) and saturated brine (20 mL) then dried over MgSO$_4$ and concentrated in vacuo to give a gummy solid. This was dissolved in methanol (3 mL) and methanolic hydrogen chloride (1 M, 4 mL) was added and stirring was continued for 18 h. The reaction mixture was concentrated in vacuo to yield a gum. This was dissolved in CH$_2$Cl$_2$ and applied to a SCX cartridge (5 g) and eluted with CH₂Cl₂:methanol, 1:1 then methanolic ammonia (1.6 M):CH₂Cl₂, 1:1 to yield N-[4-methyl-3-(1-{[4-(2,4,5-trifluorophenoxy)phenyl]methyl}(4-piperidyl))phenyl]-3-piperidylcarboxamide (88 mg, 100% yield). This was dissolved in acetonitrile (2 mL) and water (1 mL) and formaldehyde (37%, 75 μL, 0.921 mmol) followed by sodium cyanoborohydride (11 mg, 0.184 mmol) and the resulting mixture was stirred at room temperature for 1 h. This was partitioned between CH₂Cl₂ (2×10 mL) and saturated aqueous NaHCO₃ (20 mL). The combined organic layers were dried over MgSO₄ and concentrated in vacuo to yield the crude product which was applied to a SCX cartridge (5 g) and eluted with CH₂Cl₂:methanol (1:1) then methanolic ammonia to give a gum. Purification on silica (silica gel 60, ca 20 mL) eluting with CH₂Cl₂:methanol:triethylamine, 195:4:1 gave the free base as a glassy solid. This was dissolved in methanol (2 mL) and methanolic hydrogen chloride (1.25 M, 4 mL) was added. The solution was concentrated in vacuo to give (1-methyl(3-piperidyl))-N-[4-methyl-3-(1-{[4-(2,4,5-trifluorophenoxy)phenyl]methyl}(4-piperidyl))phenyl]carboxamide dihydrochloride (45 mg, 50% yield) as a gummy solid. LCMS (method A): 6.91 min, 552.3 (M+H)⁺; ¹H NMR (D₆-DMSO) δ 10.94 (br s, 1H), 10.72 (br s, 1H), 10.29 (s, 1H), 7.84 (td, J=10.8, 7.7 Hz, 1H), 7.65 (m, 2H), 7.60 (dt, J=11.0, 7.9 Hz, 1H), 7.42 (d, J=2.1 Hz, 1H), 7.38 (dd, J=8.1, 2.1 Hz, 1H,), 7.09 (m, 3H), 4.28 (d, J=5.1 Hz, 2H), 3.40 (m, 4H), 3.04 (m, 4H), 2.91 (m, 2H), 2.74 (d, J=4.8 Hz, 3H), 2.24 (s, 3H), 2.00 (m, 3H), 1.86 (m, 4H), 1.48 (m, 1H).

The following compound was prepared analogously:

Example 2b 2-(1-methyl(4-piperidyl))-N-[4-methyl-3-(1-{[4-(2,4,5-trifluorophenoxy)phenyl]methyl}(4-piperidyl))phenyl]acetamide dihydrochloride LCMS (method A): 6.83 min, 567.2 (M+H)⁺.

Example 3a

{[2-(methylamino)ethyl]amino}-N-[4-methyl-3-(1-{[4-(2,4,5-trifluorophenoxy)phenyl]methyl}(4-piperidyl))phenyl]carboxamide dihydrochloride Triphosgene was added in one portion to a solution of 4-methyl-3-(1-{[4-(2,4,5-trifluorophenoxy)phenyl]methyl}(4-piperidyl))phenylamine (100 mg, 0.235 mmol) and triethylamine (60 μL) in dry toluene (1.5 mL) at 70° C. under nitrogen. Stirring was continued at this temperature for 4 h, then allowed to cool to room temperature, diluted with diethyl ether (10 mL) and filtered through a Pall Life robotic filter funnel (1.2 mm Versapor). The filtrate was concentrated in vacuo to give 4-methyl-3-(1-{[4-(2,4,5-trifluorophenoxy)phenyl]methyl}(4-piperidyl))benzeneisocyanate (ca. 100 mg) as a colorless oil (IR: N=C=O stretch at 2261 cm⁻¹). N-(2-aminoethyl)(tert-butoxy)-N-methyl carboxamide (90 μL, 0.4 mmol) was added to a stirred solution of 4-methyl-3-(1-{[4-(2,4,5-trifluorophenoxy)phenyl]methyl}(4-piperidyl))benzeneisocyanate (90 mg, 0.2 mmol) and triethylamine (100 μL) in CH₂Cl₂ (2 mL) and stirring was continued under nitrogen for 18 h. The mixture was applied to an amino bond elute cartridge (5 g) eluting with diethyl ether, then diethyl ether:ethyl acetate (1:1) then ethyl acetate to give ({2-[(tert-butoxy)-N-methylcarbonylamino]ethyl}amino)-N-[4-methyl-3-(1-{[4-(2,4,5-trifluorophenoxy)phenyl]methyl}(4-piperidyl))phenyl]carboxamide as a cream foam (48 mg, 38% yield). LCMS (method B): 2.61 min, 627.0 (M+H)⁺. ({2-[(tert-butoxy)-N-methylcarbonylamino]ethyl}amino)-N-[4-methyl-3-(1-{[4-(2,4,5-trifluorophenoxy)phenyl]methyl}(4-piperidyl))phenyl]carboxamide was dissolved in CH₂Cl₂ (0.5 mL) and trifluoroacetic acid (0.5 mL) and stirring was continued for 30 min. The solvent was evaporated and the resulting mixture was directly applied to an amino bond elute cartridge (2 g) eluting with diethyl ether, then ethyl acetate to give the free base. This was dissolved in methanol (1 mL) and hydrochloric acid (1 M, 2 mL) was added. The resulting mixture was concentrated in vacuo to leave a gum which was triturated with diethyl ether to give {[2-(methylamino)ethyl]amino}-N-[4-methyl-3-(1-{[4-(2,4,5-trifluorophenoxy)phenyl]methyl}(4-piperidyl))phenyl]carboxamide dihydrochloride (38 mg, 87% yield) as a white solid. LCMS (method A): 6.97 min, 527.3 (M+H)⁺; ¹H NMR (D₆-DMSO) δ 10.85 (br s, 1H), 8.91 (s, 1H), 8.73 (br s, 2H), 7.84 (td, J=10.7, 7.7 Hz, 1H), 7.64 (m, 2H), 7.60 (dt, J=11.0, 7.9 Hz, 1H), 7.24 (d, J=2.2 Hz, 1H), 7.18 (dd, J=8.3 Hz, 2.2 Hz, 1H,), 7.10 (m, 2H), 7.00 (d, J=8.3 Hz, 1H), 6.58 (t, J=5.9 Hz, 1H), 4.28 (d, J=5.0 Hz, 2H), 3.38 (m, 4H), 3.07 (m, 2H), 2.97 (m, 2H), 2.91 (m, 1H), 2.55 (t, J=5.4 Hz, 3H), 2.21 (s, 3H), 2.00 (m, 2H), 1.84 (d, J=13.7 Hz, 2H).

The following compounds were prepared analogously:

Example 3b

{[2-(dimethylamino)ethyl]amino}-N-[4-methyl-3-(1-{[4-(2,4,5-trifluorophenoxy)phenyl]methyl}(4-piperidyl))phenyl]carboxamide dihydrochloride LCMS (method A): 7.63 min, 541.3 (M+H)⁺.

Example 3c

{[2-(dimethylamino)-isopropyl]amino}-N-[4-methyl-3-(1-{[4-(2,4,5-trifluorophenoxy)phenyl]methyl}(4-piperidyl))phenyl]carboxamide dihydrochloride LCMS.(method A): 7.22 min, 555.3 (M+H)⁺.

Example 3d (4-methylpiperazinyl)-N-[4-methyl-3-(1-{[4-(2,4,5-trifluorophenoxy)phenyl]methyl}(4-piperidyl))phenyl]carboxamide dihydrochloride LCMS (method A): 7.00 min, 553.3 (M+H)⁺.

Example 3e

N-[4-methyl-3-(1-{[4-(2,4,5-trifluorophenoxy)phenyl]methyl}(4-piperidyl))phenyl]piperazinylcarboxamide dihydrochloride LCMS (method A): 7.00 min, 539.3 (M+H)⁺.

Example 3f

N-[4-methyl-3-(1-{[4-(2,4,5-trifluorophenoxy)phenyl]methyl}(4-piperidyl))phenyl](pyrrolidin-3-ylamino)carboxamide dihydrochloride LCMS (method A): 7.11 min, 539.3 (M+H)⁺.

Example 4a

N-[4-methyl-3-(1-{[4-(2,4,5-trifluorophenoxy)phenyl]methyl}(4-piperidyl))phenyl](2-morpholin-4-ylethoxy)carboxamide dihydrochloride A solution of 4-methyl-3-(1-{[4-(2,4,5-trifluorophenoxy)phenyl]methyl}(4-piperidyl)) benzeneisocyanate (110 mg, 0.243 mmol), 2-morpholineethanol (44 µL, 0.366 mmol) and chloroform (10 mL) was heated at reflux for 18 h. The mixture was concentrated in vacuo and redissolved in dioxane (10 mL) and heated at reflux for 3 h. The reaction mixture was heated in the microwave at 100° C. for 10 minutes followed by a further 30 minutes. The reaction mixture was then concentrated in vacuo and purified by HPLC (5-95% acetonitrile containing 0.1% trifluoroacetic acid, over 30 min). The resulting trifluoroacetate salt was freeze dried, and redissolved in hydrochloric acid (1 M, 3 mL). The mixture was further freeze dried to give N-[4-methyl-3-(1-{[4-(2,4,5-trifluorophenoxy)phenyl]methyl}(4-piperidyl))phenyl](2-morpholin-4-ylethoxy)carboxamide dihydrochloride (15.9 mg, 11% yield) as a white solid. LCMS (method A): 6.75 min, 584.3 (M+H)$^+$; $^1$H NMR (CD$_3$OD). δ 7.61 (m, 2H), 7.40 (td, J=10.4, 7.4 Hz, 1H), 7.35 (d, J=2.0 Hz, 1H), 7.25 (m, 2H), 7.09 (m, 3H), 4.53 (m, 2H), 4.35 (s, 2H), 4.07 (d, J=13.0 Hz, 2H), 3.89 (t, J=13.0 Hz, 2H), 3.61 (t, J=13.0 Hz, 4H), 3.54 (m, 2H), 3.24 (m, 4H), 3.12 (m, 1H), 2.31 (s, 3H), 2.03 (m, 4H).

Example 5a

N-[4-methyl-3-(1-{[4-(2,4,5-trifluorophenoxy)phenyl]methyl}(4-piperidyl)) phenyl][(2-morpholin-4-ylethyl)amino]carboxamide dihydrochloride Phenyl chloroformate (118 µL, 0.938 mmol) and pyridine (114 µL, 1.407 mmol) were added to a stirred solution of 4-methyl-3-(1-{[4-(2,4,5-trifluorophenoxy)phenyl]methyl}(4-piperidyl))phenylamine (200 mg, 0.469 mmol) in dry CH$_2$Cl$_2$ (5 mL). The resulting mixture was heated at reflux for 5 h then concentrated in vacuo. The residue was purified on a bond elute cartridge (10 g—performed twice) eluting with CH$_2$Cl$_2$:methanol (19:1) to give N-[4-methyl-3-(1-{[4-(2,4,5-trifluorophenoxy)phenyl]methyl}(4-piperidyl))phenyl]phenoxycarboxamideridyl))phenyl]carboxamide (140 mg, 54% yield).

LCMS (method B): 3.01 min, 547.0 (M+H)$^+$.

N-[4-methyl-3-(1-{[4-(2,4,5-trifluorophenoxy)phenyl]methyl}(4-piperidyl))phenyl]phenoxy carboxamideridyl))phenyl]carboxamide (70 mg, 0.128 mmol) was dissolved in dioxane (5 mL) and 4-(2-aminoethyl)morpholine (34 µL, 0.25 mmol) was added. The resulting mixture was heated at reflux for 20 h, and concentrated in vacuo to give the crude product. Purification by HPLC (2-95% acetonitrile over 30 min) yielded the triflouroacetate salt, which was dissolved in hydrochloric acid (1 M, 3 mL) and freeze dried to give N-[4-methyl-3-(1-{[4-(2,4,5-trifluorophenoxy)phenyl]methyl}(4-piperidyl)) phenyl][(2-morpholin-4-ylethyl)amino]carboxamideyl))phenyl]carboxamide dihydrochloride (37.5 mg, 45% yield) as a white solid. LCMS (method A): 7.39 min, 583.3 (M+H)$^+$; $^1$H NMR (CD$_3$OD) δ 7.59 (m, 2H), 7.40 (td, J=10.4, 7.5 Hz, 1H), 7.25 (m, 2H), 7.18 (dd, J=8.2, 2.3 Hz, 1H), 7.09 (m, 3H), 4.35 (s, 2H), 4.06 (m, 2H), 3.82 (m, 2H), 3.62 (m, 6H,), 3.31 (t [hidden under CHD$_2$OD], 2H), 3.18 (m, 4H), 3.10 (m, 1H), 2.31 (s, 3H), 2.03 (m, 4H).

Example 5b was prepared analogously:

Example 5b

N-[4-methyl-3-(1-{[4-(2,4,5-trifluorophenoxy)phenyl]methyl}(4-piperidyl))phenyl][(2-pyrrolidinylethyl)amino]carboxamide dihydrochloride LCMS (method A): 7.00 min, 567.4 (M+H)$^+$.

Example 6a

{[2-(dimethylamino)ethyl]methylamino}-N-[4-methyl-3-(1-{[4-(2,4,5-trifluorophenoxy)phenyl]methyl}(4-piperidyl))phenyl]carboxamide dihydrochloride A mixture of 4-methyl-3-(1-{[4-(2,4,5-trifluorophenoxy)phenyl]methyl}(4-piperidyl)) phenylamine (54 mg, 0.126 mmol), p-nitrophenyl chloroformate (51 mg, 0.25 mmol) and pyridine (31 µL, 0.378 mmol) in dry CH$_2$Cl$_2$ (3 mL) was heated at reflux for 5 h. The reaction mixture was concentrated in vacuo and the residue was triturated with pentane to give as N-[4-methyl-3-(1-{[4-(2,4,5-trifluorophenoxy)phenyl]methyl}(4-piperidyl))phenyl](4-nitrophenoxy)carboxamide as a white solid (93.2 mg, quantitative crude yield). LCMS (method B): 2.77 min, 592.0 (M+H)$^+$. A suspension of N-[4-methyl-3-(1-{[4-(2,4,5-trifluorophenoxy)phenyl]methyl}(4-piperidyl))phenyl](4-nitrophenoxy) carboxamide 43.2 mg, 0.073 mmol) and N,N,N-trimethyl ethylenediamine (20 µL, 0.146 mmol) in dioxane (1.5 mL) was heated in the microwave at 100° C. for 10 min. The reaction mixture was concentrated in vacuo to yield the crude product, which was purified by HPLC (5-95% acetonitrile containing 0.1% trifluoroacetic acid, over 30 min) then freeze dried to give the impure trifluoroacetate salt. This was dissolved in aqueous hydrochloric acid (1 M, 3 mL), and concentrated in vacuo. The residue was partitioned between ethyl acetate (30 mL) and aqueous saturated NaHCO$_3$ (saturated, 30 mL) and the organic layer was washed with aqueous NaCl (saturated, 30 mL) then dried over MgSO$_4$ and concentrated in vacuo to give the impure free base. This was further partitioned between aqueous hydrochloric acid (1 M, 30 mL) and ethyl acetate (30 mL). The aqueous layer was basified with aqueous saturated NaHCO$_3$ then extracted with ethyl acetate (30 mL). The combined organic layers were dried over MgSO$_4$ and concentrated in vacuo to yield the purified free base. To this was added hydrochloric acid (1 M, 3 mL) and the resulting mixture was concentrated in vacuo and freeze dried to give {[2-(dimethylamino)ethyl]methylamino}-N-[4-methyl-3-(1-{[4-(2,4,5-trifluorophenoxy)phenyl]methyl}(4-piperidyl))phenyl]carboxamide dihydrochloride (31 mg, 67% yield) as a white solid. LCMS (method A): 6.60 min, 555.3 (M+H)$^+$; $^1$H NMR (CD$_3$OD) δ 7.60 (m, 2H), 7.40 (td, J=10.4, 7.5 Hz, 1H), 7.34 (d, J=2.2 Hz, 1H), 7.25 (dt, J=10.8, 7.8 Hz, 1H), 7.17 (1H, dd, J=8.2, 2.2 Hz, 1H), 7.09 (m, 3H), 4.34 (s, 2H), 3.73 (t, J=5.7 Hz, 2H), 3.59 (m, 2H), 3.35 (t, J=5.7 Hz, 2H), 3.18 (m, 2H), 3.11 (m, 4H), 2.98 (s, 6H), 2.32 (s, 3H), 2.05 (m, 4H).

Example 7a 4-methyl-3-(1-{[4-(2,4,5-trifluorophenoxy)phenyl]methyl}(4-piperidyl)) phenylamine N-[4-methyl-3-(1-{[4-(2,4,5-trifluorophenoxy)phenyl]methyl}(4-piperidyl))phenyl](phenylmethoxy)carboxamide (4.88 g, 8.68 mmol) was dissolved in ethanol (150 mL) and hydrogenated over palladium on carbon (10%, 980 mg) for 2.5 h. The reaction mixture was filtered through celite filter aid, washing with ethanol and the filtrate was concentrated in vacuo. Flash column chromatography (silica gel 60) eluting with cyclohexane:ethyl acetate (1:1 then 1:4) provided 4-methyl-3-(1-{[4-(2,4,5-trifluorophenoxy)phenyl]methyl}(4-piperidyl))phenylamine (3.71 g, 100%). LCMS (method B): 2.14 min, 427.0 (M+H)$^+$; $^1$H NMR (400 MHz, CD$_3$OD) δ 7.63 (d, 2H, J=7.2 Hz), 7.41-7.33 (m, 2H), 7.27-7.23 (m, 2H), 7.15 (d, 1H, J=8.0 Hz), 7.09 (d, 2H, J=8.0 Hz), 4.36 (s, 2H), 3.61 (d, 2H, J=12.0 Hz), 3.22 (t, 3H, J=12.0 Hz), 2.42 (s, 3H), 2.15-2.02 (m, 4H).

Example 7b 3-(1-{[4-(3,4-difluorophenoxy)phenyl]methyl}(4-piperidyl))-4-methylphenylamine LCMS (method A): 6.84 min, 409.0 (M+H)$^+$.

Example 7c 5-(1-{[4-(3,4-difluorophenoxy)phenyl]methyl}(4-piperidyl))-2-fluoro-4-methylphenylamine LCMS (method A): 8.45 min, 427.2 (M+H)$^+$.

Example 7d 5-(1-{[4-(3,4-difluorophenoxy)phenyl]methyl}-4-piperidyl)-3-pyridylamine LCMS (method A): 6.75 min, 396.2 (M+H)$^+$.

Example 7e 6-methyl-5-(1-{[4-(2,4,5-trifluorophenoxy)phenyl]methyl}(4-piperidyl))-3-pyridylamine LCMS (method A): 5.87 min, 428.2 (M+H)$^+$.

Example 7f 3-(1-{[4-(3,4-difluorophenoxy)phenyl]methyl}(4-piperidyl))-2,4,6-trifluorophenylamine LCMS (method A): 8.65 min, 449.2 (M+H)$^+$.

Example 7g 5-(1-{[4-(3,4-difluorophenoxy)phenyl]methyl}(4-piperidyl))-2,4-difluorophenylamine LCMS (method A): 8.97 min, 431.3 (M+H)$^+$.

Example 7h 2-fluoro-4-methyl-5-(1-{[4-(2,4,5-trifluorophenoxy)phenyl]methyl}(4-piperidyl))phenylamine LCMS (method A): 8.45 min, 445.2 (M+H)$^+$.

Example 7i 2,4-difluoro-5-(1-{[4-(2,4,5-trifluorophenoxy)phenyl]methyl}(4-piperidyl))phenylamine LCMS (method A): 8.97 min, 449.2 (M+H)$^+$.

Example 7j 5-(1-{[4-(2,4,5-trifluorophenoxy)phenyl]methyl}-4-piperidyl)-3-pyridylamine LCMS (method A): 6.70 min, 414.2 (M+H)$^+$.

Example 7k 2,4,6-trifluoro-3-(1-{[4-(2,4,5-trifluorophenoxy)phenyl]methyl}(4-piperidyl))phenylamine LCMS (method A): 8.62 min, 467.2 (M+H)$^+$.

Example 7l 5-(1-{[4-(3,4-difluorophenoxy)phenyl]methyl}(4-piperidyl))-6-methyl-3-pyridylamine LCMS (method A): 5.85 min, 410.3 (M+H)$^+$.

Formulations

The pharmaceutical formulations of the invention may be prepared by conventional methods in the art.

For example, tablets may be prepared by mixing the active ingredient with ordinary adjuvants and/or diluents and subsequently compressing the mixture in a conventional tabletting machine may prepare tablets. Examples of adjuvants or diluents comprise: corn starch, potato starch, talcum, magnesium stearate, gelatine, lactose, gums, and the like. Any other adjuvants or additives usually used for such purposes such as colorings, flavorings, preservatives etc. may be used provided that they are compatible with the active ingredients.

1) Tablets containing 5.0 mg of Compound 1 k calculated as the free base:

| | |
|---|---|
| Compound 1k | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of Compound 1 k calculated as the free base:

| | |
|---|---|
| Compound 1k | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing 25 mg of Compound 1 k per milliliter:

| | |
|---|---|
| Compound 1k | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |

| -continued | |
|---|---|
| Flavor | 0.05 mg |
| Saccharin | 0.5 mg |
| Water | 1 mL |

In Vitro Methods

The pharmacological properties of the compounds of the present invention were evaluated at the cloned rat MCH1 receptor using the protocols disclosed in U.S. Pat. No. 6,727,264, the contents of which are hereby incorporated by reference.

Using this protocol, the inhibition by the compound of the binding of a radiolabeled ligand (tritiated SNAP-7941) to membranes harvested from CHO cells expressing cloned rat MCH1 receptors was determined in vitro. The radiochemical synthesis of tritiated SNAP-7941 was performed by Amersham Pharmacia Biotech, Cardiff, Wales.

Briefly, the affinity of the compounds was measured by their ability to displace tritiated SNAP-7941 from rat MCH1 expressing membranes. The compound and radioligand were incubated with the membranes at 25° C. for 90 min. Incubation was terminated by rapid vacuum filtration over GF/C glass fiber filters, presoaked in 5% PEI using 50 nM Tris pH 7.4 as wash buffer. In all experiments, nonspecific binding was defined using 10 pM of tritiated SNAP-7941.

The binding affinities for the compounds in the present invention, exemplified above, at the MCH1 receptor were determined to be 200 nM or less. For the majority of the compounds, the Ki values are 100 nM or less, and for a large group of compounds the Ki values are 10 nM or less.

The invention claimed is:

1. A compound of the structure:

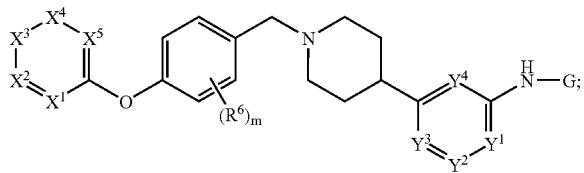

wherein each $X^1, X^2, X^3, X^4$ and $X^5$ is independently $CR^1$;
wherein each $Y^1, Y^2, Y^3$ and $Y^4$ is independently $CR^7$;
wherein G is —C(O)D;
wherein D is

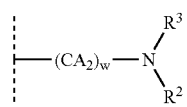

wherein each A is independently H or straight chained or branched $C_1$-$C_4$ alkyl;

wherein each $R^1$ is independently H, straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein $R^2$ is H or straight chained or branched $C_1$-$C_4$ alkyl;

wherein $R^3$ is H or straight chained or branched $C_1$-$C_4$ alkyl;

wherein each $R^6$ is independently straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein each $R^7$ is independently H, straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein m is an integer from 0 to 4 inclusive; and wherein w is an integer from 1 to 5 inclusive;

or a pharmaceutically acceptable salt thereof.

2. The compound of claim 1, wherein m is 0 or 1, and $R^6$ is methyl, F or Cl.

3. The compound of claim 2, wherein each $R^1$ is independently H, methyl, F or Cl, and each $R^7$ is independently H, F or methyl.

4. The compound of claim 3, wherein w is 1 or 2, and $R^3$ is H, methyl or ethyl.

5. The compound of claim 4, wherein $R^2$ is H, methyl or ethyl.

6. A pharmaceutical composition comprising a therapeutically effective amount of a compound of claim 1 and a pharmaceutically acceptable carrier.

7. A compound selected from the group consisting of 2-(methylamino)-N-[4-methyl-3-(1-{[4-(2,4,5-trifluorophenoxy)phenyl]methyl}(4-piperidyl))phenyl]acetamide, 2-(dimethylamino)-N-[4-methyl-3-(1-{[4-(2,4,5-trifluorophenoxy)phenyl]methyl}(4-piperidyl))phenyl]acetamide dihydrochloride, 3-(dimethylamino)-N-[4-methyl-3-(1-{[4-(2,4,5-trifluorophenoxy)phenyl]methyl}(4-piperidyl))phenyl]propanamide, (2S)-3-methyl-2-(methylamino)-N-[4-methyl-3-(1-{[4-(2,4,5-trifluorophenoxy)phenyl]methyl}(4-piperidyl))phenyl]butanamide, (2S)-2-(methylamino)-N-[4-methyl-3-(1-{[4-(2,4,5-trifluorophenoxy)phenyl]methyl}(4-piperidyl))phenyl]propanamide, 2-(ethylamino)-N-[4-methyl-3-(1-{[4-(2,4,5-trifluorophenoxy)phenyl]methyl}(4-piperidyl))phenyl]acetamide and N-(4-methyl-3-(1-{[4-(2,4,5-trifluorophenoxy)phenyl]methyl}(4-piperidyl))phenyl](2-propylamino)acetamide.

* * * * *